(12) United States Patent
Kanowitz

(10) Patent No.: US 11,471,631 B2
(45) Date of Patent: *Oct. 18, 2022

(54) AIRWAY STABILIZATION SYSTEM

(71) Applicant: Securisyn Medical, LLC, Highlands Ranch, CO (US)

(72) Inventor: Arthur Kanowitz, Littleton, CO (US)

(73) Assignee: Securisyn Medical, LLC, Littleton, CO (US)

( * ) Notice: Subject to any disclaimer, the term of this patent is extended or adjusted under 35 U.S.C. 154(b) by 345 days.

This patent is subject to a terminal disclaimer.

(21) Appl. No.: 16/113,046

(22) Filed: Aug. 27, 2018

(65) Prior Publication Data

US 2019/0070378 A1 Mar. 7, 2019

Related U.S. Application Data

(60) Provisional application No. 62/551,028, filed on Aug. 28, 2017.

(51) Int. Cl.
*A61M 16/04* (2006.01)

(52) U.S. Cl.
CPC .... *A61M 16/0497* (2013.01); *A61M 16/0418* (2014.02); *A61M 16/0463* (2013.01); *A61M 16/0434* (2013.01); *A61M 2205/584* (2013.01); *A61M 2210/0625* (2013.01)

(58) Field of Classification Search
CPC .. A61M 16/00; A61M 16/04; A61M 16/0463; A61M 16/0488; A61M 16/049; A61M 16/0493; A61M 16/0497; A61M 16/08; A61M 16/0816; A61M 16/0875
See application file for complete search history.

(56) References Cited

U.S. PATENT DOCUMENTS 3,774,616 A * 11/1973 White ............... A61M 16/0497
128/200.26
10,463,822 B2 * 11/2019 Kanowitz ......... A61M 16/0497
(Continued)

*Primary Examiner* — Joseph D. Boecker
(74) *Attorney, Agent, or Firm* — Glenn H. Lenzen; Elevated IP, LLC

(57) ABSTRACT

An airway stabilization system including an airway device and a securing mechanism or faceplate therefor is provided which includes active stabilizing components on both the airway device and the faceplate which prevent clinically significant movement of the airway device with respect to the patient's vocal cords in response to the application of significant forces in any direction to the device, be they longitudinal, torsional/rotational or bending. The system includes an airway device and an attached retention collar which interacts with a securing device/patient to ensure proper airway insertion depth and provide unparalleled strength and stability against movement. The airway stabilization system includes a unique stabilizer readily adapted for use in field situations to releasably engage or release a retention structure on the airway device to facilitate ease of application in all conditions, a twist-off 15 mm connector which allows a secure connection of the 15 mm connector to the airway device while facilitating easy disconnection thereof, and a universal bite block which cooperates with the securing system to prevent oral and/or dental damage and discomfort to the patient when the system is installed.

20 Claims, 21 Drawing Sheets

(56) References Cited

U.S. PATENT DOCUMENTS

| | | | |
|---|---|---|---|
| 2007/0083262 A1* | 4/2007 | Matlock | A61M 16/0427 |
| | | | 623/9 |
| 2010/0154800 A1* | 6/2010 | Chang | A61M 16/04 |
| | | | 128/207.15 |
| 2011/0284008 A1* | 11/2011 | Kanowitz | A61M 16/0488 |
| | | | 128/207.17 |
| 2012/0006330 A1* | 1/2012 | Barbot | A61M 16/0816 |
| | | | 128/207.14 |
| 2012/0247477 A1* | 10/2012 | Stephenson | A61M 16/0816 |
| | | | 128/207.14 |
| 2016/0095995 A1* | 4/2016 | Haider | A61M 16/0493 |
| | | | 128/207.14 |
| 2016/0279367 A1* | 9/2016 | Kanowitz | A61M 16/0497 |
| 2018/0133423 A1* | 5/2018 | Bateman | A61M 16/0497 |
| 2021/0128860 A1* | 5/2021 | Van Der Vegt | A61M 25/02 |

* cited by examiner

AIRWAY STABILIZATION SYSTEM

CROSS REFERENCE TO RELATED APPLICATIONS

This application claims the benefit of U.S. Provisional Patent Application No. 62/551,028 filed Aug. 28, 2017, the entire disclosure of which is incorporated herein by reference.

FIELD OF THE INVENTION

The present invention relates generally to human and veterinary medical devices. Specifically, the present invention relates to an airway stabilization system designed to maintain an airway device in a preselected position in the trachea of a human patient or an animal and for preventing clinically significant movement thereof and unintentional extubation of the patient or animal in response to the application of significant multidirectional forces to the airway device. More specifically, the system of the present invention relates to a safe and effective airway device or endotracheal tube apparatus (ETT) that enables precise positioning thereof in an airway and a securing device adapted to cooperatively interact with the improved airway device to facilitate rapid and simple insertion of the airway device, particularly in emergency and/or field situations, and rapid and secure coupling and uncoupling thereof to a source of ventilatory air.

BACKGROUND OF THE INVENTION

Endotracheal intubation is a medical procedure used to place an airway device (artificial airway) into a patient's trachea or airway. The use of an airway device is mandated in situations where an individual, or an animal in veterinary applications, is unable to independently sustain the natural breathing function or maintain an open airway due to unconsciousness, trauma, disease, drugs or anesthesia. Thus, life-saving mechanical ventilation is provided through the airway device, which may be in the form of an endotracheal tube (ETT), or a supraglottic airway device such as a laryngeal mask airway (LMA), King Airway, or one of several other commercially available airway devices.

Endotracheal intubation is accomplished by inserting an airway device into the mouth, down through the throat and larynx, and into the trachea. This procedure creates an artificial passageway through which air can freely and continuously flow in and out of a patient's lungs and prevents the patient's airway from collapsing or occluding.

It is very important that the airway device be positioned correctly and maintained in the correct position in the trachea. If the device moves out of its proper position in the trachea and into either the right or left main stem bronchial tube, only one lung will be ventilated. Failure to ventilate the other lung can lead to a host of severe pulmonary complications. Moreover, if the airway device moves completely out of the trachea and into the pharynx, esophagus or completely outside the body, the patient will become hypoxic due to the lack of ventilation to the lungs, a condition which typically results in life-threatening brain injury within a matter of only a few minutes.

Even after an airway device has been positioned correctly, subsequent movement of the patient can lead to inadvertent movement of the device, as hereinabove described. An intubated patient may restlessly move about and may also attempt to forcibly remove an airway device, whether conscious or subconscious, particularly if the patient is uncomfortable or having difficulty breathing, which can lead to panic. In the case of an animal patient, agitation may be particularly pronounced due to the animal's lack of cognitive awareness or understanding of its circumstances and an instinctual survival fight or flight response. A large animal or a carnivore can pose a serious danger not only to itself but also to a treating veterinarian and anyone in close proximity under such circumstances.

Medical emergencies may occur anywhere. Accordingly, emergency medical service personal (i.e., paramedics) may be called upon to insert airway devices in out-of-hospital emergency settings, for example at accident scenes, and military personnel in combat situations, in emergency response vehicles, as well as in hospital settings by emergency department physicians, anesthesiologists, and critical care clinicians. Therefore, such unintentional movement of either the patient or an airway device is not uncommon, particularly when the patient is moved from an out-of-hospital setting, such as any one of the afore-mentioned scenarios, to an emergency department of a hospital. Further, anytime an intubated patient is be moved, for example, not only from an ambulance to a trauma facility, but also from one hospital to another hospital, from one area of the hospital to another area in the same hospital (imaging, laboratory, operating theater), or from a hospital to an outpatient rehabilitation facility, unintentional movement of an airway device is a risk. Even repositioning an intubated patient in a hospital bed, or in the case of an animal, in a recovery cage, may cause unintentional movement of the endotracheal tube.

Inadvertent movement of an airway device may also occur as a result of moving external ventilation equipment, such as a conventional mechanical ventilator or bag valve mask. Typically, the external ventilation equipment is connected to the external end of the device by an air conduit to establish air flow to and from the lungs. Inadvertent pulling on, or other excessive movement of the air conduit, may not only disconnect it from the airway device, but may also transfer movement to the airway device, thereby shifting it from its proper position and causing unplanned extubation.

Unplanned extubation is a hazardous and costly problem in humans, a problem which studies have established occurs at an unacceptably high rate. For example, Statistics published by the Society for Critical Care Medicine states that in 2017 there were 1.65 Million intubated, mechanically ventilated ICU patients in the United States (Medicine, S.f.C.C. Critical Care Statistics 2017). A review of the world-wide medical literature suggests that the world-wide rate of unplanned extubation averages approximately 7.31% of extubated patients. Lucas de Silva, *Unplanned Endotracheal Extubation in the Intensive Care Unit: Systematic Review, Critical Appraisal, and Evidence-Based Recommendations*. Anesth Analg 2012; 114:1003-14. Applying the world-wide average to the U.S. figure above, an estimated 120,000 patients in the United States alone experience an unplanned extubation each year. Such unplanned extubations are costly, not only for patients who experience increased rates of morbidity and mortality, but also for hospitals, physicians and insurance companies who incur the liability costs associated therewith. The annual intensive care unit (ICU) bed cost associated with unplanned extubations in the United States alone is estimated at $4.9 Billion, which includes imaging, pharmacy, and laboratory expenses. (Extrapolated using data from the Carson study referenced above and the cost of long-term care according to the U.S. Department of Health and Human Services National Clearinghouse for long-term care information. See also S. K. Epstein, M. L. Nevins & J. Chung, *Effect of Unplanned Extubation on Outcome of Mechanical Ventilation*, Am. Journal of Respiratory and Critical Care Medicine, 161: 1912-1916 (2000) which discusses the increased likelihood of long-term care outcome). Moreover, it is not unknown for jury damage awards in personal injury law suits arising from unplanned extubations to be in excess of $35 M.

Clearly, the economic losses related to unintentional extubation of animals are not as serious as the well-documented economic losses in human cases. Nonetheless, economic losses in the agricultural sector of valuable farm animals, breeding stock, and food resources, particularly in underdeveloped countries, cannot be ignored. On the domestic side, as anyone who has lost a beloved pet can attest, the emotional pain can equal that experienced at the loss of a family member. In view of the foregoing, the high incidence of unplanned extubation and the associated increase in healthcare costs implies that an improved restraining system is sorely needed, a system which has the capacity to resist the application of forces which would otherwise result in movement of the airway device.

Various prior art systems have attempted to address the problem of maintaining an airway device in the correct position and preventing unintentional extubation. The most common approach for securing an airway device (typically, an endotracheal tube) is with adhesive tape. Umbilical tape may be used as an alternative. Both present the same challenges. The tape is tied around the patient's neck and then wrapped and tied around the smooth outside surface of the endotracheal tube itself. Arranged in this fashion, the tape is intended to anchor the endotracheal tube to the corner of the patient's mouth and prevent its unintentional movement. While the use of tape in this manner provides some benefit, the restraint available from the tape usually diminishes because the tape becomes covered and/or saturated with blood, saliva, or other bodily fluids. Consequently, the endotracheal tube may be readily moved from its preferred position in a patient's trachea. In spite of its widespread use, adhesive or surgical tape is woefully inadequate in providing protection against movement resulting from the application of multidirectional forces such as bending, torsional/rotational or substantial lateral forces to the device, forces which may exceed fifty (50) pounds in magnitude.

The results of two studies of the restraint capabilities of current devices and methods are set forth in Tables 1 and 2 below. Such devices and methods do not provide sufficient resistance to prevent unplanned extubation. Clinically significant movement is defined as longitudinal movement of the airway device in a direction towards or away from the patient's mouth to a point where the tip of the airway device has moved beyond the larynx or vocal cords. Typically, such movement in a human patient is in the range of five (5) to seven (7) centimeters. In an animal, it may be significantly more or less, depending upon the size of the animal. For example, clinically significant movement in a cat is considerably less than clinically significant movement in a long-necked animal such as a horse or a giraffe.

Restraint Capabilities of Current Devices and Methods in Human Applications

TABLE 1

|  | Median | Min | Max |
| --- | --- | --- | --- |
| Thomas Tube Holder | 12.98 | 2.64 | 22.44 |
| Adhesive Tape | 19.58 | 3.96 | 39.6 |
| Non-Adhesive Tape | 7.48 | 2.42 | 27.72 |

Force to Extubate (7 cm movement) in Lbs
Owens, et al. Resuscitation (2009)

TABLE 2

|  | Median | Min | Max |
| --- | --- | --- | --- |
| Adhesive Tape (Lillehei) | 19.5 | 15 | 25 |
| Tube Tamer | 12.9 | 10 | 15 |
| Precision Medical | 8.6 | 7 | 10 |
| Biomedix Endogrip | 10.7 | 6 | 12 |
| Thomas Tube Holder | 37 | 28 | 43 |

Force to Extubate (2 cm movement) in Lbs
Carlson, et al. Annals of Emergency Medicine 2007

In the human medical field, efforts to address the foregoing problems have resulted in apparatus such as disclosed in U.S. Pat. No. 5,353,787 issued Oct. 11, 1994, to Price. Price discloses an apparatus having an oral airway for providing fluid communication for the passage of gas from a patient's mouth through his or her throat and into the trachea, the oral airway being releasably attached to an endotracheal tube for use in combination therewith. While Price's apparatus eliminates the smooth surface of the tube and resists longitudinal movement in relation to the oral airway, his system does not address the above-identified problem of resisting multidirectional forces. Moreover, Price's device cannot prevent clinically significant movement of an airway device in relation to the vocal cords and an unplanned extubation resulting therefrom.

Other attempts to solve the aforementioned problems have employed auxiliary mechanical securing devices to maintain the position of an endotracheal tube in a patient. Many of these auxiliary mechanical devices include some type of plate which is attached to the patient's face, usually with one or more straps that extend around the back of the patient's head or neck. The faceplate includes some type of mechanical contact device that grips the smooth surface of the endotracheal tube. Typical mechanical contact devices include thumb screws, clamps, adhesives, locking teeth, and straps. By way of example, U.S. Pat. No. 4,832,019 issued to Weinstein et al. on May 23, 1989, discloses an endotracheal tube holder which includes a hexagonally-shaped gripping jaw that clamps around the tube after it has been inserted into a patient's mouth and a ratchet-type locking arrangement designed to retain the gripping jaw in position around the tube. Weinstein's patent disclosure states specifically that the tube will not be deformed. However, the fundamental mechanics of a hexagonal receptacle applied around a cylindrical tube to stabilize it reveal that the hexagonal structure will not impart force to the tube of sufficient magnitude to prevent longitudinal movement. However, it has been found that if sufficient pressure is applied directly to the tube by the gripping jaw, the tube will deform or even crush, thereby decreasing ventilatory efficiency to the point that airflow to the patient's lungs will be restricted or even cut off, an extremely serious problem.

U.S. Pat. No. 7,568,484 issued on Aug. 4, 2009, and U.S. Pat. No. 7,628,154 issued on Dec. 8, 2009, both to Bierman et al., disclose endotracheal tube securement systems which include straps extending from the corners of a patient's mouth above and below the patient's ears on each side of the patient's head. However, the devices disclosed in the '484 and the '154 patents merely retain the position of the tube in the patient's mouth and cannot prevent movement thereof in various directions, either longitudinally, rotationally or laterally, as hereinabove described.

Specifically, to maintain an effective restraint, attending medical personnel increase the amount of clamping force applied on an airway device. Increasing the amount of clamping force to an effective level may pinch the device to the point where a portion of the inner tube diameter (and hence air passageway) is significantly restricted. Restricting the cross-sectional size of the air passageway decreases the ventilatory efficiency of the tube, thereby decreasing the respiratory airflow. The restriction of the cross-sectional size of the air passageway creates resistance to both inspiratory airflow and expiratory airflow. Insufficient airflow during inspiration can lead to hypoxemia, which is problematic, but can be overcome by increasing the positive pressure of the ventilation source. However, during expiration, any increased pressure due to constriction or decreased tube diameter, increases the amount of work a patient must perform to simply exhale. Increased pressure can also lead to barotrauma in the lungs and resistance to expiratory airflow can lead to multiple other adverse effects within the lungs. Impairing a patient's ventilations may result in serious medical effects, particularly with patients whose functions are already compromised. Therefore, the ability for clinicians to adequately stabilize an airway device for prevention of unplanned extubation without constriction of the air passageway is crucial for patient safety.

In addition to the foregoing, other issues have arisen with respect to standard respiratory connectors that serve as conduits between the endotracheal tube and artificial ventilator for the purpose of maintaining a continuous flow of air from the ventilation source to the patient's lungs. Standard connectors must be tightly seated into the endotracheal tube to avoid unintentional disconnection of the ventilation source from the endotracheal tube during mechanical breathing. When tightly seated, the connector is often difficult for the clinician to remove from the endotracheal tube, when necessary. Therefore, an airway device with a connector that prevents unintentional disconnection, yet allows for quick and easy intentional connection and disconnection is needed.

More recently, U.S. Pat. No. 8,001,969 issued on Aug. 23, 2011, and U.S. Pat. No. 8,739,795 issued on Jun. 3, 2014, both to Arthur Kanowitz, the inventor of the present invention, disclose airway stabilization systems which address many of the problems set forth above. Continuing research into ways of providing even more advanced and rapidly deployable airway stabilization systems have resulted in yet further improvements to the overall design of the system components, which, as can be seen from the following, are also may be used to address analogous problems in the veterinary medical field.

Maintaining an endotracheal tube in an animal's airway during surgery or emergency trauma situations is just as critical to the wellbeing of an animal as it is to a human patient. However, in one sense, the anatomical structure of many animals may allow an endotracheal tube to be secured to an animal patient more easily than might be possible for a human patient. For example, U.S. Patent Application Publication No. US 2004/0154622 A1 published by Davis on Aug. 12, 2004, discloses an endotracheal tube apparatus for treating an animal patient having a tie which is used to literally tie the tube to either the animal's upper or lower jaw. Such ties are offered commercially by Trinity Trach-Tube Ties, Ft. Worth, Texas and consist of plastic ties that may be tied around an airway device before insertion of the device into an animal's mouth and trachea and then tied around the animal's muzzle. Unlike surgical tape, the Trinity ties are made of plastic and do not become saturated with body fluids in use.

A variation of the plastic tie approach is disclosed in U.S. Patent Application Publication No. US 2014/0102458 A1 published by Landow et al., Apr. 17, 2014, for a plastic tube tie which may be fastened to either an endotracheal tube or an anesthesia mask and then either tied behind an animal patient's neck or head or around its muzzle. Plastic ties in accordance with the Landow et al. disclosure are offered commercially by Jorgensen Laboratories, Inc., Loveland, Colo. Alternatively, a muzzle such as one disclosed by Taylor in U.S. Pat. No. 8,596,224 B2 which issued on Dec. 3, 2013, combines the features of wrapping a restraint around an animal's muzzle with Landau's plastic tube which may be fastened behind an animal's neck or head. However, these approaches to safe intubation of an animal patient may work adequately only while the animal is sedated but are not designed or structured to safely maintain an airway device on an animal if it awakes, particularly if it is a frightened or agitated emotional state.

In view of the above, it will be apparent to those skilled in the art from this disclosure that a need exists for an improved airway stabilization system which not only protects an airway device from occlusion and crushing, but also is easier to apply to a patient while at the same time maintains the device in its preferred position in a patient's trachea and prevents clinically significant movement thereof with respect to the vocal cords as a result of the application of multidirectional forces of significant magnitude thereto. The present invention addresses these needs in the art as well as other needs, all of which will become apparent to those skilled in the art from the accompanying disclosure.

SUMMARY OF THE INVENTION

In order to address the aforementioned needs in the art, a complete airway stabilization system is provided which may be fitted to any airway device that may be used with human patients or with animal patients in veterinary applications to maintain an airway in a human or animal patient's trachea. The stabilization system prevents clinically significant movement of the airway device with respect to a patient's vocal cords in response to the application of forces in any direction to the device, be they longitudinal, torsional/rotational or bending.

Unlike conventional prior art devices which employ an airway device that is passive in the stabilization process, for example, a passive endotracheal tube and an active stabilizer, the system disclosed herein comprises an airway device (endotracheal tube or supraglottic airway device) that is active in the stabilization process and which cooperates with a securing apparatus or stabilizer that is also active in the stabilization process. Both devices have active stabilization components that cooperate integrally with and engage one another to provide unparalleled strength and stability against movement, even when the endotracheal tube becomes slippery from fluids and/or secretions without applying any constricting pressure whatsoever to the airway device itself.

The airway device has a flexible elongate body which conforms to a patient's trachea after it is installed in the patient and includes a continuous sidewall extending between a proximal and a distal end portion thereof, thereby a hollow conduit through which the airway is established. A retention member or collar is positioned on the exterior of the sidewall of the airway device between the end portions thereof at a predetermined fixed position relative to the distal end of the airway device and outside of a patient's oral cavity so as to minimize risk of oral and/or dental injury to the patient. The retention collar includes a plurality of spaced-apart alternating ribs and structural recesses extending circumferentially about the body of the collar. The ribs provide an active surface area forming a tight interlocking fit with cooperating interlocking flanges and structural recesses of a stabilizer apparatus secured to the patient, thereby establishing a complete barrier against movement which would otherwise result from forces applied to the device as hereinabove described.

In an embodiment, a securing apparatus or stabilizer includes a plate or faceplate which is secured to the patient and a tower structure operatively connected thereto which is configured to cooperate with the interacting retention collar to prevent clinically significant movement of the distal end of the airway device with respect to the vocal cords of the patient. The faceplate is formed of a single member to allow greater ease of application, the member being structured and arranged to be secured over the face of a patient and being operatively connected to the restraining tower while, at the same time, providing ease of access to the patient's oral cavity for administration of medications and oral hygiene.

The tower structure is secured to the plate and extends outwardly therefrom in a direction away from a patient's face. The restraining tower includes a pair of oppositely disposed pivotally interconnected c-shaped Collars, each collar including a plurality of a plurality of substantially uniformly spaced-apart annular flanges positioned axially along the inner surface of the body portion and extending substantially inwardly therefrom, a plurality of structural recesses positioned axially along the inner surface of the body portion intermediate an adjacent two of the plurality of substantially uniformly spaced-apart annular flanges the ribs and structural recesses of the retention collar operatively interacting with the annular flanged and structural recesses of the restraining tower to retain the airway device via releasable engagement with the retention member secured thereto.

In an embodiment, a universal bite block is provided which is adopted to be positional in a patient's oral cavity adjacent an airway device to prevent crushing of the airway device if the patient attempts to bite down on the tube.

In yet another embodiment, the universal bite block is operatively connected to the securing apparatus.

In still another embodiment the universal bite block is formed internally with the securing apparatus.

In another embodiment, at least one of the plurality of ribs formed on the retention structure is marked to distinguish it from the other ribs, and one of the pivotally interconnected c-shaped collars includes a plurality of spaced apart depth indicator markings formed thereon, the markings being structured and arranged to cooperate with at least one marked rib formed on the retention structure to indicate the relative position of the retention structure with respect to the position of the restraining device the marked rib.

In still another embodiment, the airway device includes an inflatable cuff or balloon secured to a distal end of thereof and a plurality of reflective locator bands proximally positioned with respect to the balloon on and extending circumferentially around the flexible elongate body of the airway device.

In an embodiment, a securing apparatus is provided which may be installed and/or removed from an airway device positioned previously in a patient's airway without interrupting ventilation of the patient.

In yet another embodiment, an endotracheal tube assembly is provided that further includes a locking mechanism that is adapted to quickly and releasably secure a respiratory or 15 mm connector to the endotracheal tube assembly via a simple twisting motion These and other features, aspects and advantages of the present invention will become apparent to those skilled in the art from the following detailed description of preferred embodiments taken in connection with the accompanying drawings, which are briefly summarized below, and by reference to the appended claims.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
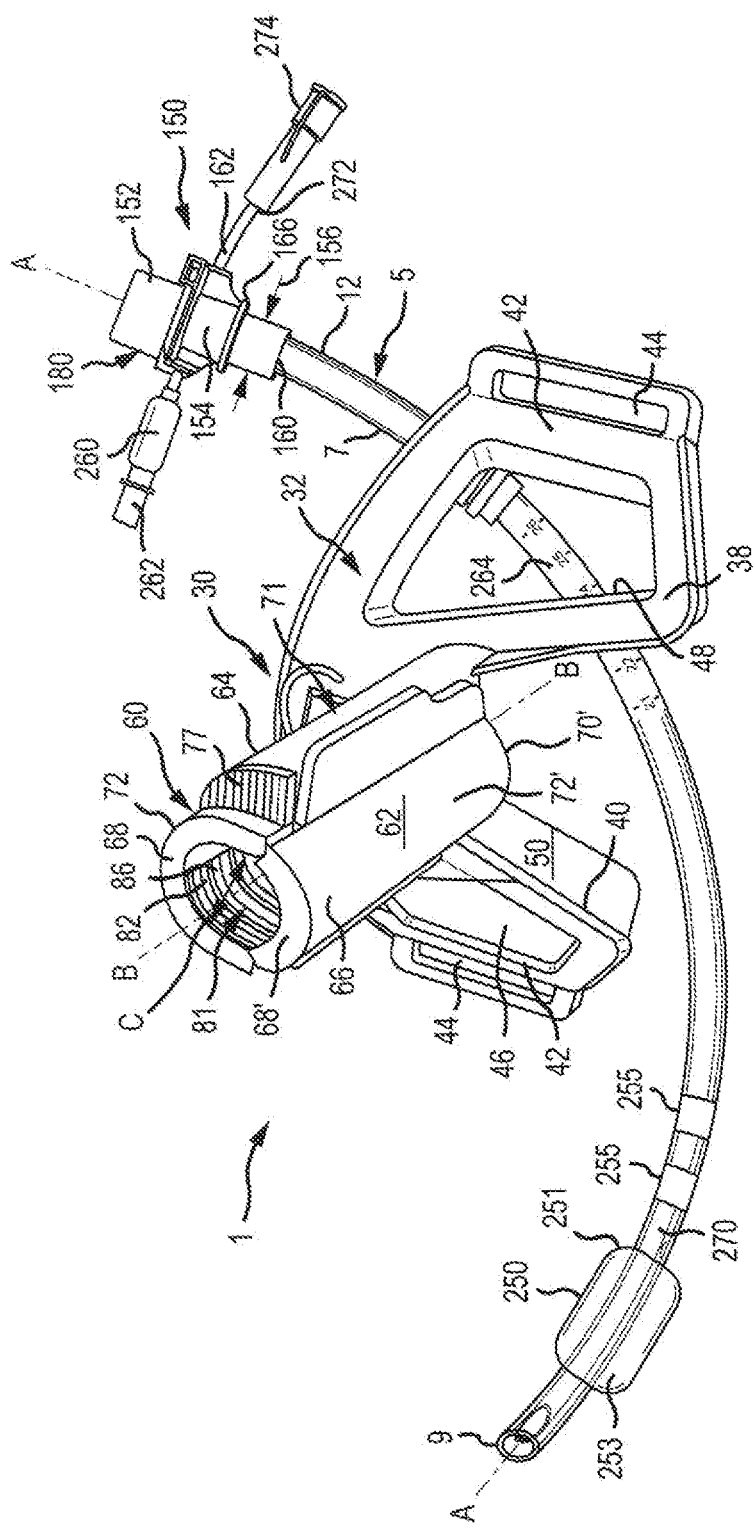
FIG. 1 is a side perspective view of the elements of an airway stabilization system according to an embodiment of the present invention.
Figure 6:
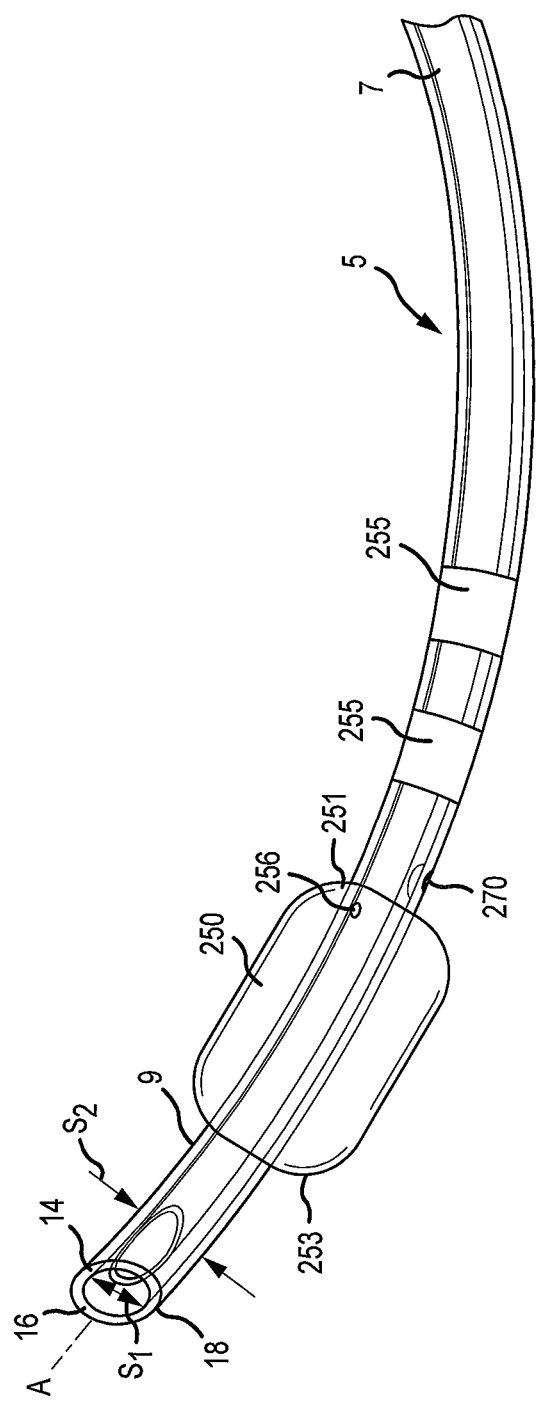
FIG. 6 is a side elevation view of the distal end of an airway device showing an inflatable cuff or balloon secured thereto and a pair of reflective locator bands proximally positioned on the flexible body portion of the airway device in accordance with an embodiment.

Referring initially to FIGS. 1 and 6, an airway stabilization system shown generally at numeral 1 is illustrated in accordance with an embodiment of the present invention. The airway stabilization system is used to maintain an airway in a human (or animal patient in veterinary applications) under conditions where natural respiration is impossible or severely compromised. The airway stabilization system includes an airway device depicted generally at 5 which has a flexible elongate body 7 extending along an axis A-A and having a length, an internal diameter $S_1$ and an external diameter $S_2$, a distal end portion 9, a proximal end portion 12 and a continuous sidewall 14 having an internal surface 16 and an external surface 18 extending between the proximal and the distal ends.

The airway stabilization system also includes a securing apparatus 30, the airway device and securing apparatus cooperating to maintain an air passageway to a patient's lungs via the patient's mouth, oral cavity, throat, past a patient's vocal cords or larynx into a patient's trachea and to a patient's carina (the point where the trachea bifurcates into the bronchial tubes) for respiration of the patient. By way of example and not of limitation, the airway device may be in the form of an endotracheal tube (ETT) as shown in the accompanying figures, one of several commercially available endotracheal tubes or one of several commercially available supraglottic airway devices such as a King LT™ airway device manufactured by King Systems, Noblesville, Ind. or a laryngeal mask airway (LMA) such as a LMA Classic™ manufactured by LMA North America, San Diego, Calif.

Figure 2:
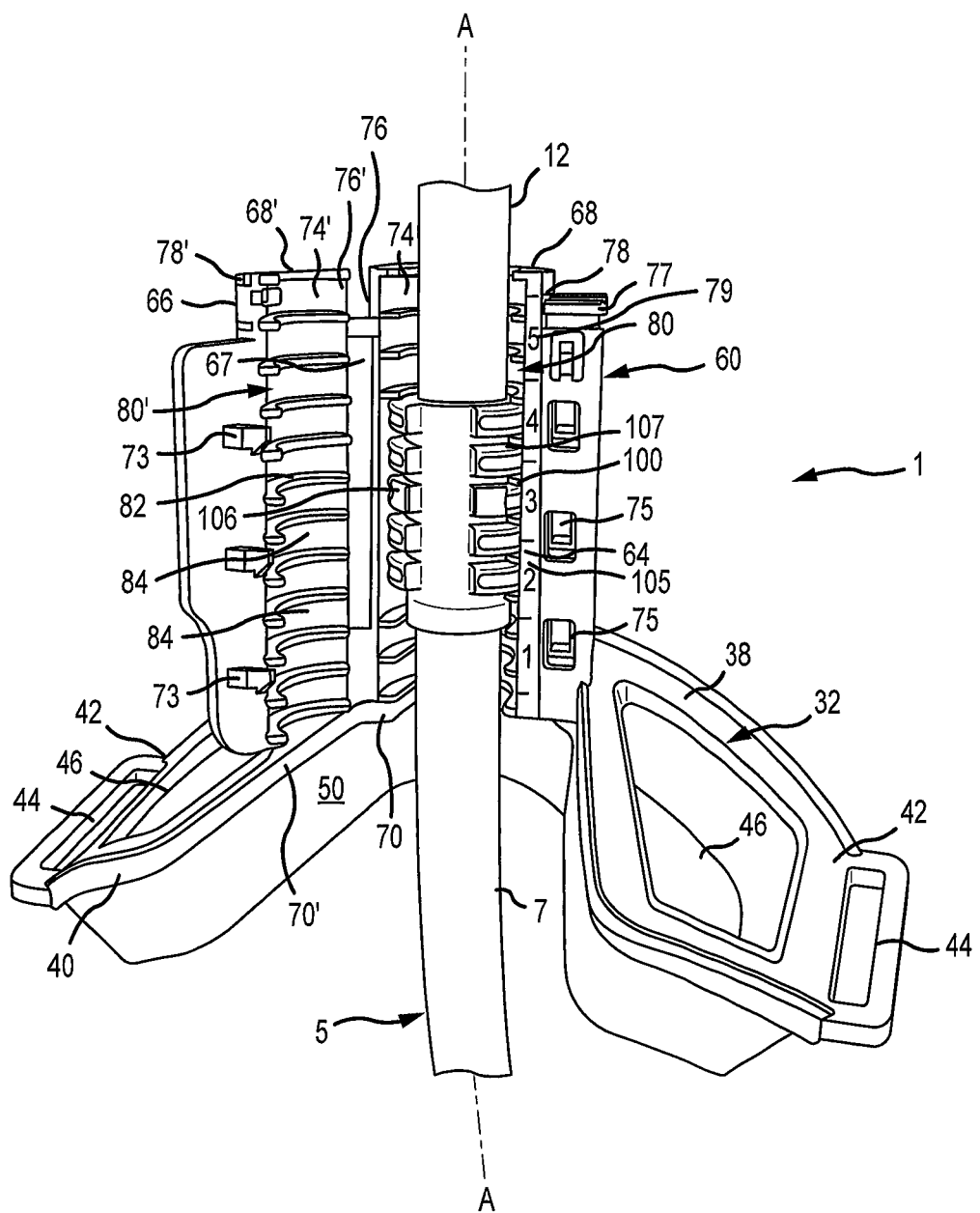
FIG. 2 is a side perspective view of a securing apparatus or stabilizer of an airway stabilization system of the embodiment of FIG. 1 shown in an open position to more clearly illustrate the elements thereof.
Figure 3:
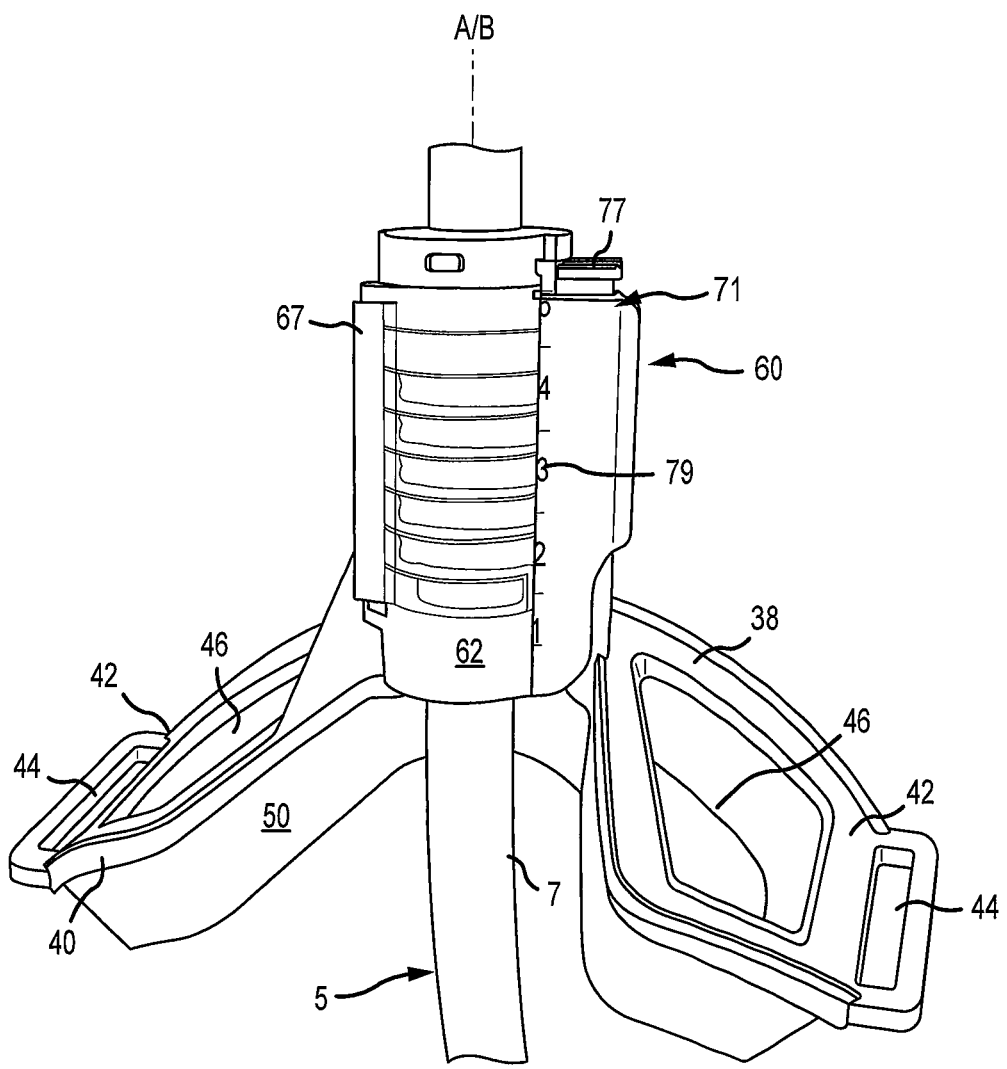
FIG. 3 is a side perspective view of a securing apparatus or stabilizer of an airway stabilization system of the embodiment of FIG. 1 shown in a closed position to more clearly illustrate the elements thereof.
Figure 14:
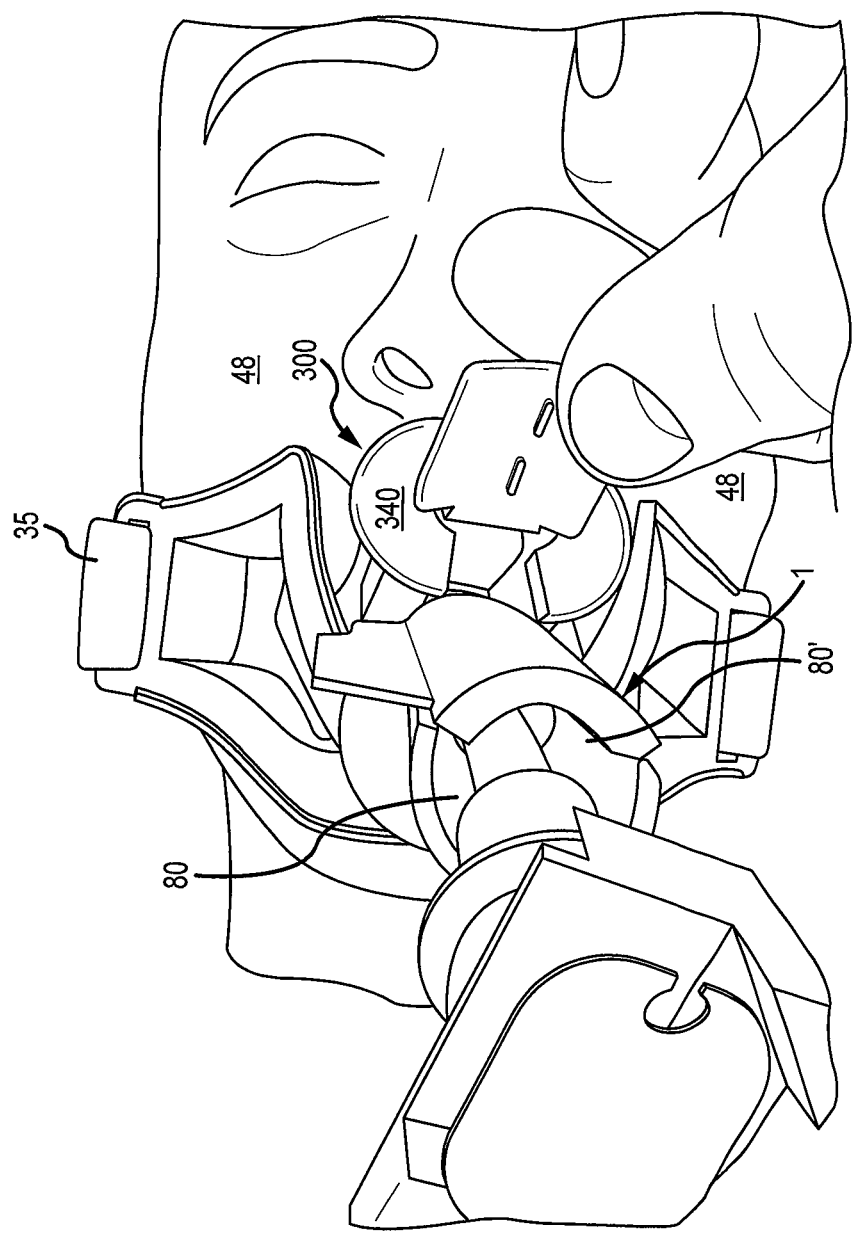
FIG. 14 is a top view of an airway stabilization system and bite block of the present invention partially installed on a patient.
Figure 15:
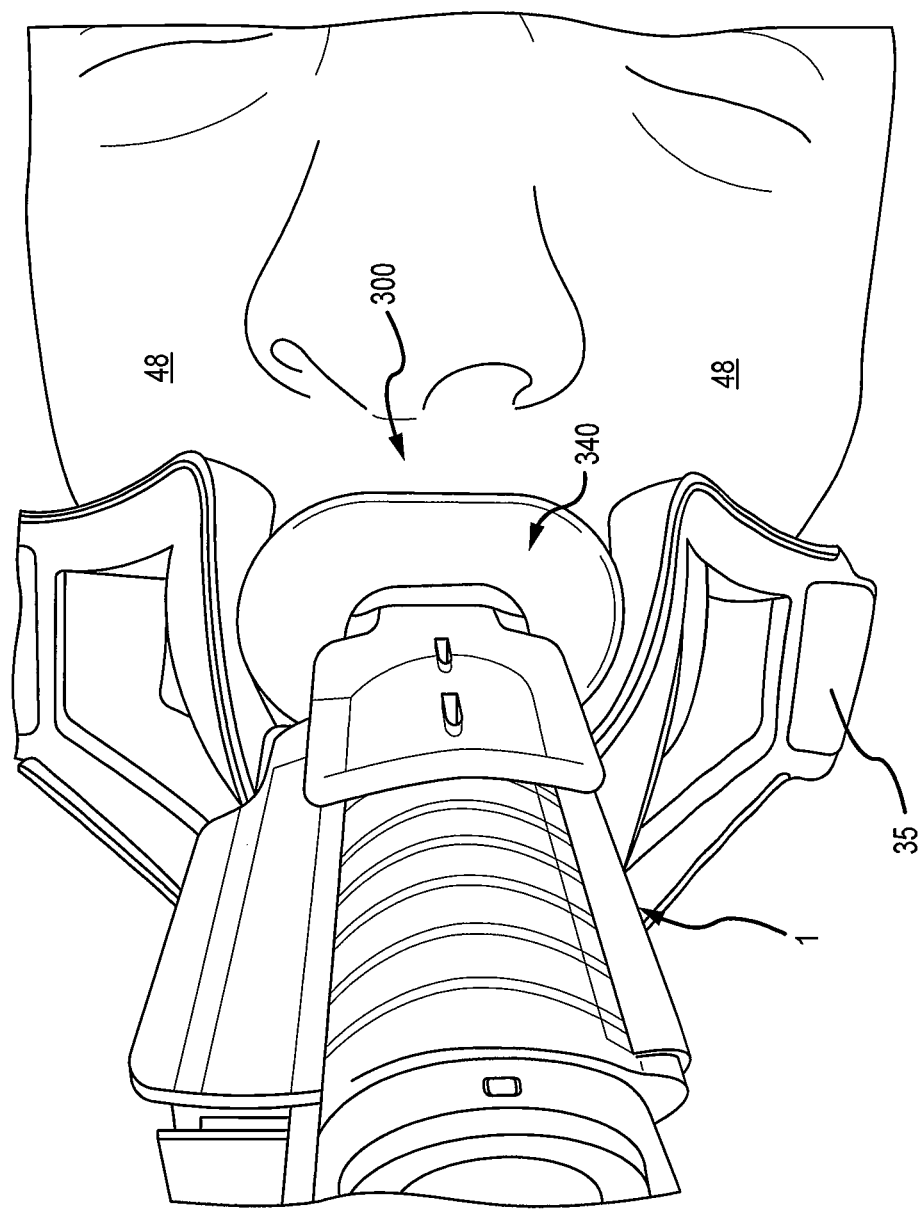
FIG. 15 is a top view of the airway stabilization system and bite block shown in FIG. 14 installed on a patient.

Referring to FIGS. 2 and 3, a portion of the airway stabilization system is depicted in greater detail. The securing apparatus 30 includes a plate or faceplate 32 which may be secured to the patient's face by a suitable attachment apparatus, by way of example and not of limitation, a strap 35 (FIGS. 14 and 15) extending around the patient's head and securable by buckles, Velcro or other suitable attachments, as is known in the art. The plate is preferably of unitary construction and in a generally symmetrical mask-like configuration contoured to permit it to conform to a patient's face when it is secured in position. It may be formed of plastic, rubber, metal, composite material or other suitable materials having the desired physical properties for the application. The faceplate 32 includes an upper or top (maxillary) surface 38, an oppositely disposed lower or bottom (mandibular) 40 surface, the upper and lower surfaces being interconnected by a pair of oppositely disposed, spaced apart end portions 42, each end portion having an aperture or slot 44 formed therein and adapted to receive securing apparatus 35. The plate or faceplate includes apertures 46 adapted to be positioned over a patient's respective cheek areas 48, as shown in FIGS. 14 and 15, thus allowing the device to fit over a patient's face like a mask as described above while yet permitting access to the patient's face, mouth and oral cavity for administering medications and performing oral hygiene. The plate is generally symmetric about a patient's oral cavity and nose, thereby facilitating ease of positioning thereof on a patient's face and may also include a cushioning material or layer 50 secured to the lower surface to provide additional comfort for the patient.

Referring again to FIG. 1, the securing apparatus 30 includes a generally cylindrically-shaped tower structure 60 extending in a substantially perpendicular direction from the top surface 38 of the plate 32 along axis B-B, the tower structure including a body portion 62 having a length and comprising a pair of oppositely disposed, pivotally interconnected, c-shaped collars 64, 66 respectively extending generally symmetrically about and along the axis in a direction away from the patient's face when installed on a patient, each of the collars having a length, first and second end portions 68, 68' and 70, 70', an outer surface 72, 72', an inner surface 74, 74'. Each of the outer and inner surfaces extends intermediate the c-shaped collars' respective first and second end portions. Each of the collars has a pair of generally parallel extending edge surfaces 76, 78 and 76', 78', the edge surfaces and the corresponding c-shaped collar each defining an opposed, semi-cylindrically shaped cavity 80, 80' about the axis B-B. These cavities are most clearly shown in FIG. 2 from the side and in FIG. 14 from the top.

Each c-shaped collar includes a plurality of substantially uniformly spaced-apart annular flanges 82 positioned axially along the respective inner surfaces thereof and extending substantially inwardly therefrom, and a plurality of structural recesses 84 positioned axially along each inner surface intermediate an adjacent two of the plurality of substantially uniformly spaced-apart annular flanges, each one of the plurality of annular flanges cooperating with an adjacent one of the plurality of annular flanges to define one of the plurality of structural recesses. Each of the annular flanges has an aperture 86 formed therein, each aperture being adapted to receive the airway device and a retention member when installed thereon, as will be described in greater detail below.

Figure 4:
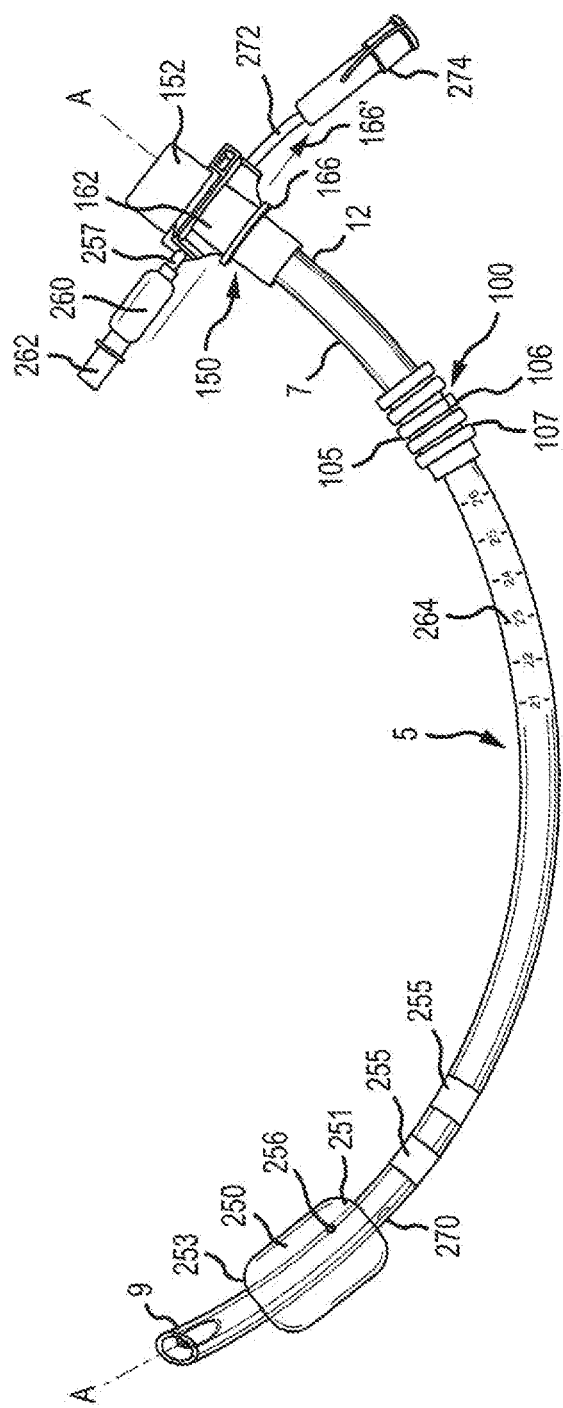
FIG. 4 is a side perspective view of an airway device in accordance with an embodiment.

Referring to FIGS. 2 and 4, the airway stabilization system 1 of the instant invention further includes a retention member or collar 100 positioned on and secured to the airway device 5 and extending circumferentially about and coaxially along the body portion 7 of the airway device. The retention member has a length and includes a plurality of substantially uniformly spaced-apart ribs 105 positioned axially along the length of the retention member and extending radially outwardly therefrom. The retention member further includes a plurality of structural recesses 107 positioned axially along the length of the retention member, each of the plurality of structural recesses being positioned intermediate an adjacent two of the plurality of spaced-apart ribs In operation. the collars 64 and 66 are pivotally interconnected, for example, by hinge member 67 and are moveable into mating contact with one another, thereby forming a cavity 81 defined by the opposed semi-cylindrically shaped cavities 80, 80; the cavity having an inner diameter C and being adapted to releasably engage and enclose the retention member secured to the airway device, such that axis A-A of the airway device extends coaxially along axis B-B of the cylindrically shaped tower structure 60, as best illustrated in FIG. 3. Each of the c-shaped collars includes a snap, clip, latch, camming operating apparatus or other suitable interlocking feature 71 having one or more locking members 73 adapted to releasably engage corresponding mating locking members 75 formed in or secured to the other c-shaped collar to releasably clamp them together circumferentially around the airway device in stabilizing and supporting engagement therewith. A release mechanism, for example, a quick-release actuator or button 77, allows the c-collars to be easily and rapidly released from locking engagement with one another to facilitate positioning and adjustment of the plate 32 and cylindrically-shaped tower structure with respect to the retention member. Once the airway device is positioned at the desired depth in a patient's trachea, the strap 35 of the securing apparatus is secured around the patient's head. A plurality of spaced apart reference markings or depth guides 79 are formed on c-collar 64 which are structured and arranged to cooperate with other features of the system for ease of monitoring the relative position of the airway device with respect to the restraining tower, as defined more specifically below. For example, one or more of the plurality of ribs formed on the retention structure, by way of example, the middle rib 106, is marked to distinguish it from the other of the plurality of ribs formed thereon. The marked rib may be aligned by the attending practitioner with an appropriate one of the depth guides 79 to assist in inserting the airway device to a desired depth in the patient's trachea.

When the c-collars 64 and 66 are locked together as show in FIG. 3, the inwardly extending annular flanges 82 and structural recesses 84 on the inner surfaces of the of the c-shaped collars releasably engage corresponding mating structural recesses 107 and outwardly extending spaced-apart ribs 105 of the retention member, thereby creating multiple points of contact and interaction between the securing apparatus and the airway device and thus preventing clinically significant movement of the airway device in response to substantial forces which may be applied thereto in any direction. The retention structure and securing apparatus cooperate to completely enclose the airway device whereby the airway device is isolated totally from any constricting, pinching, or crushing forces that would constrict an inner diameter thereof, thereby also restricting ventilation of a patient. Advantageously, in accordance with an embodiment of the instant invention, unlike prior art securing devices, the system herein disclosed may be secured laterally from a side of an airway device without being placed over the end of the device and, therefore, without disconnecting a ventilation source or interrupting ventilation of a patient.

Figure 7:
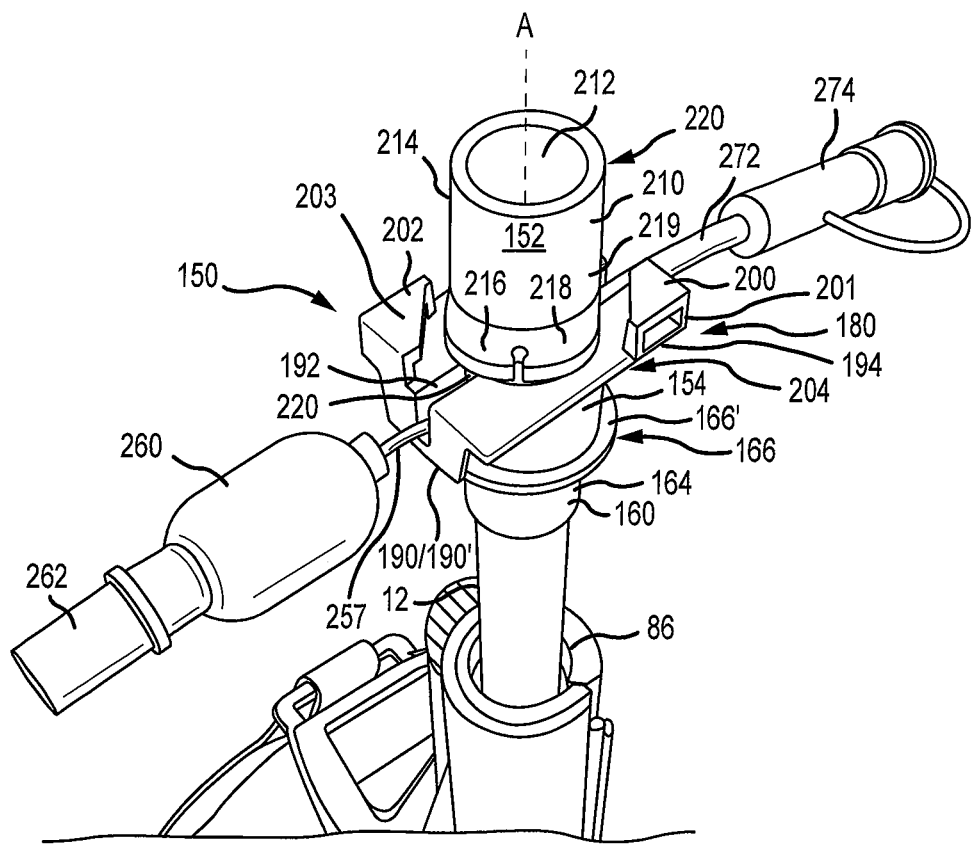
FIG. 7 is a top perspective view of a connector assembly adapted to connect a respiratory connector to the airway device accordance with an embodiment.
Figure 8:
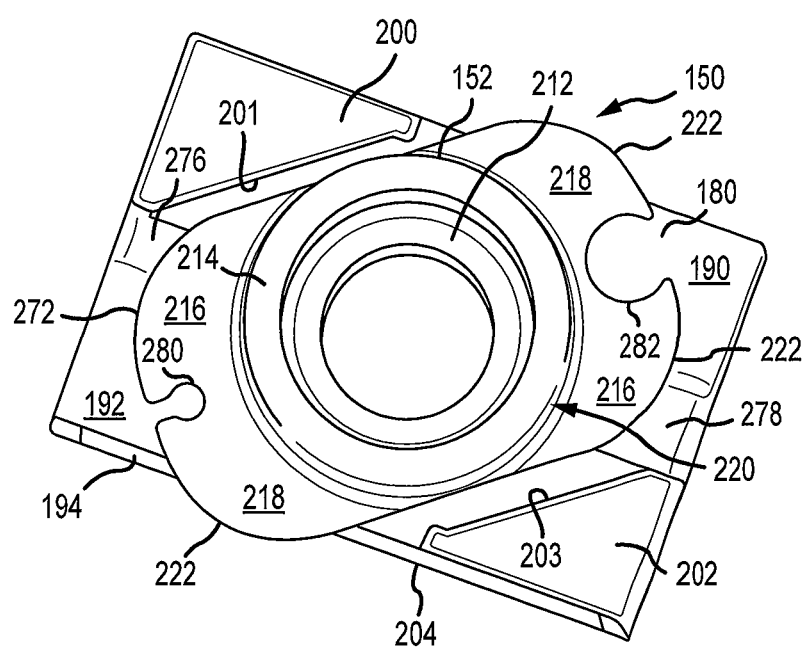
FIG. 8. is a top plan view of the connector assembly shown in FIG. 7 illustrating the assembly in an unlocked position in accordance with an embodiment.
Figure 9:
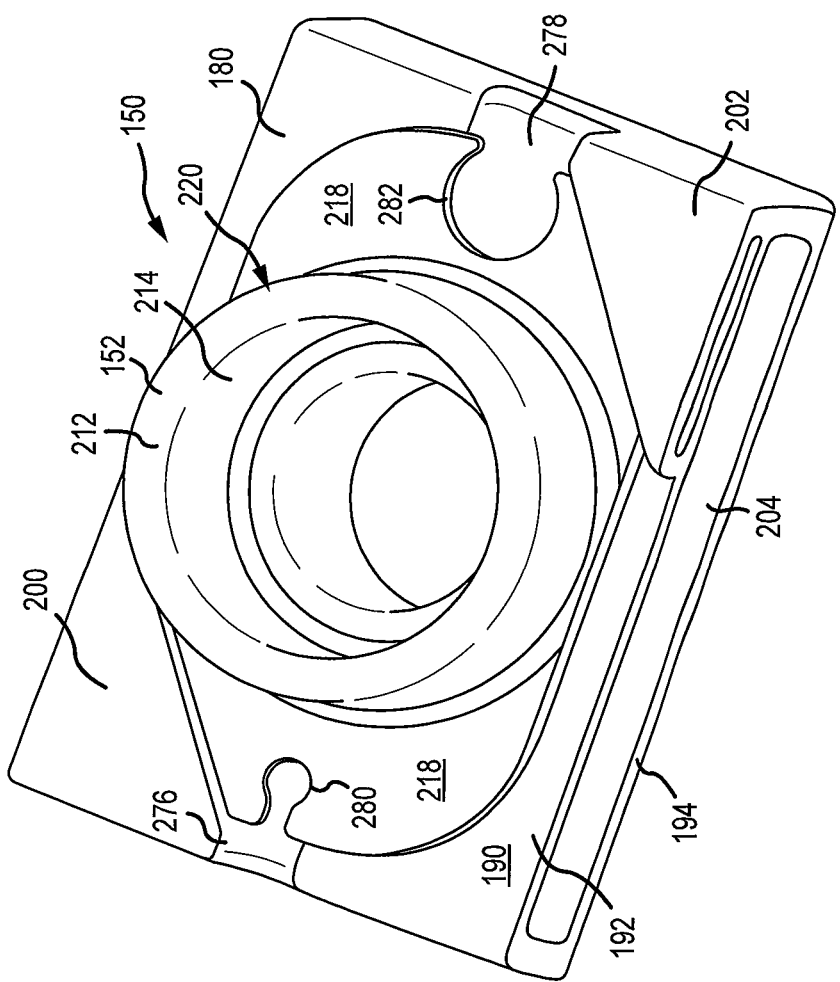
FIG. 9 is a side elevation view of the connector assembly shown in FIGS. 7 and 8 illustrating the assembly in a locked position in accordance with an embodiment.

Referring now to FIGS. 1 and 4, and, more specifically, to FIGS. 7, 8 and 9, the details of a connector assembly or safety connector complex 150 are described in greater detail. The connector assembly is operatively connected to the proximal end 12 of the elongate body of the airway device and is adapted to connect a respiratory connector, also referred to as a 15 mm connector, 152 to the airway device. The connector assembly includes body 154 extending along the axis A-A and having a length, an internal diameter and an external or outer diameter 156, a distal end 160 adapted to receive the proximal end 12 of the airway device, a proximal end 162 adapted to receive the respiratory connector 152, a continuous sidewall 164 extending between the proximal and the distal ends, and a stop member or safety stop 166 extending radially outwardly from the continuous sidewall. In the embodiment shown, the safety stop is in the form of a ring or a flange 166 extending circumferentially around 166 the continuous sidewall 166 of the connector assembly body and defining a first plane 166' which is substantially perpendicular to the axis A-A, the flange having an outer diameter which is larger than the outer diameter 156 of the connector assembly body. The ring has a diameter which is larger than the diameter C of the cavity 81. The safety stop prevents the airway device from being positioned too low in the cavity 81, which could cause the retention member or collar 100 to enter a patient's oral cavity and potentially cause trauma to the patient's teeth or oral tissue.

Referring to FIG. 7, the connector assembly further includes a locking device 180 secured to the proximal end 162, the locking device being structured and arranged to releasably secure the respiratory connector 152 to the connector assembly. The locking device includes a plate member 190 having an upper surface 192 and a lower surface 194, the lower surface being secured to the proximal end 162 of the connector assembly, the upper surface including first and second locking channels or pockets 200, 202 attached thereto, each pocket having aperture 201, 203 respectively extending substantially perpendicular to and diagonally across the upper surface of the plate. The locking device further includes a centrally-positioned aperture (not shown) extending intermediate the upper and lower surfaces 192, 194 along the axis A-A, the aperture having a diameter of approximately the same size as the external diameter $S_2$ of the airway device. The plate member 190 defines a second plane 190' which is substantially perpendicular to the axis A-A and positioned proximally above the first plane 166' of the stop member, the plate member further including an edge surface 204 extending intermediate the upper and lower surfaces of the plate member in a direction substantially parallel to the axis A-A.

As shown in FIG. 7, the respiratory connector 152 comprises a tubular member 210 having an air passage 212 extending therethrough along the axis A-A, a proximal end 214 configured to be secured to a source of ventilatory air, a pair of diagonally positioned locking flanges 216, 218 extending radially outwardly from the proximal end defining a third plane 219 which is substantially perpendicular to the axis, and a distal or connector end 220 extending distally along the axis from the locking flanges and operatively connected thereto, the connector end 220 being adapted to be removably inserted into the proximal end 162 of the connector assembly. In operation, as best viewed in FIGS. 7 and 8, the distal end 220 of the respiratory connector is inserted into the aperture in the proximal end of the connector assembly with the locking flanges generally aligned diagonally across the upper surface of the plate 190 and parallel to the faces 201, 203 of the respective locking channels. After the respiratory connector is fully inserted, it is rotated in a clockwise direction until each of the locking flanges 216 is positioned in one of the respective pockets 200, 202 as shown in FIG. 9, and a source of ventilatory air is then connected to the air passage 212 via tubular member 210. The flanges 216 and 218 are symmetrically positioned with respect to the central axis A-A and each are separated by a rounded corner 222 to facilitate rotational insertion of either of the flanges into the locking pockets.

Turning now to FIGS. 1 and 4-6, the details of an embodiment of an airway device 5 of the present invention are shown in greater detail. As described earlier, the airway device comprises an endotracheal tube which has a flexible elongate body 7 extending along an axis A-A and having a length, an internal diameter $S_1$ and an external diameter $S_2$ (FIG. 6), a distal end portion 9, a proximal end portion 12 and a continuous sidewall 14 having an internal surface 16 and an external surface 18 extending between the proximal and the distal ends. The proximal end 12 is sized and configured to mate with the distal end 160 of the connector assembly 150.

As shown in the enlarged illustration of a portion of the apparatus in FIG. 6, the airway device includes an inflatable cuff or balloon 250 having a proximal end 251 and a distal end 253 secured to the distal end 9 thereof and a plurality of reflective locator bands 255 proximally positioned with respect to the balloon on and extending circumferentially around the flexible elongate body of the airway device. The reflective locator bands are formed of a highly visible material, such as a white paint, which renders the bands highly visible to a clinician as the airway device is being positioned in a patient's trachea. An inflation tube 257, which may extend along the outside surface of the tube or, alternatively, may be located within the tube's continuous sidewall 14, extends from an inflation lumen 256 formed in the airway device sidewall 14 inside the balloon to a balloon inflation pilot 260 (which indirectly indicates the pressure in the balloon) and then via connecting line or tube 262 to a source of inflationary air. A plurality of insertion depth reference markers or indicators 264 are affixed to the midbody and cooperate with the reflective locator bands 255 in facilitating accurate positioning of the airway device. The indicators are luminescent in color, for example, a bright white, instead of the conventional light-absorbing black. The bright luminescent color readily reflects the light of a light source such as a laryngoscope, thereby making the bands highly visible in a patent's airway. Suction lumen 270 is positioned in the continuous sidewall 14 near the proximal end 251 of the balloon and is connected via a suction line 272, which, like the inflation line, may extend along the outside surface of the tube or, alternatively, may be located within the tube's continuous sidewall 14, to a connector 274 and then to a suction apparatus. The plate 190 of the locking apparatus has a channel 276 formed upper surface 192 thereof and extending in a direction substantially parallel to edge surface 204, the channel being structured and arranged to receive the inflation tube and to protect it from damage during use. A second channel 278 is formed in upper surface 192 opposite channel 276 and is similarly adapted to receive the suction line for purposes of preventing damage thereto when the stabilization system is installed on a patient. Channels 276 and 278 cooperate with flanges 216 and 218 to prevent the inflation and suction lines from being accidentally crushed and effectively increase the amount of force that would be required to damage or remove the tubes, either of which would render the balloon and/or the suction unit non-functional. Keyhole slots 280 and 282 formed intermediate each of the diagonally positioned locking flanges 216, 218 are adapted to receive the inflation and suction lines respectively and cooperate with the slots in protecting the lines after the respiratory connector is rotated into locking engagement with the respective locking channels 200, 202.

Referring to FIGS. 10-15, the elements and operation of a universal bite block 300 are shown. The bite block is adapted for use with the airway stabilization system of the present invention as well as with other airway systems and airway devices in both human and veterinary medical applications. The bite block includes a thin flat member or panel 304 defining a plane 304' having substantially perpendicular longitudinal and transverse axes B-B and C-C; the panel including an upper surface 310, a lower surface 312, and a circumferential edge surface 316 connected to and extending between the upper and lower surfaces, the circumferential edge surface including a pair of spaced-apart first and second longitudinal edge portions 320, 322 extending parallel to the longitudinal axis, a pair of spaced-apart first and second transverse edge portions 326, 328 extending parallel to the transverse axis; and a transversely extending flange shown generally at 340. As depicted in FIGS. 14 and 15, when the bite block is installed in a patient's oral cavity, the flange 340 rests against the patient's upper lip to prevent the bite block from being inserted too deeply. A first support member 345 is secured to and extends along one of the pair of longitudinal edges, and a second support member 348 is secured to and extends along the other of the pair of longitudinal edges.

The flange includes a c-shaped body 350 connected to the bite block, the c-shaped body including an upper surface 352 and a lower surface 354 and an elongate portion 356 (FIG. 12) extending in a transverse direction substantially parallel to the transverse axis across the upper surface 310 of the panel and in a transverse plane 356' extending through the plane 304' defined by the panel in a direction perpendicular thereto. The c-shaped body further includes first and second legs 358, 360 lying in the transverse plane and forming the short portions of the letter c-shaped body. The first leg 358 is connected to a first end 362 of the elongate portion of the c-shaped body, to one of the pair of spaced-apart longitudinal edges 320 and to the lower surface of the plate. The second leg 360 is operatively connected to a second end 364 of the elongate portion of the c-shaped body, to the other of the pair of spaced-apart longitudinal edges 322 and to the lower surface of the panel. A space 368 extending transversely across the lower surface of the panel intermediate the first and second legs separates the two legs, thereby cooperating with the elongate portion 356 in forming the c-shape of the stop member. The first traverse edge portion 328 is located at a distance $d_1$ from the lower surface 354 of the C-shaped body of the stop member.

Each of the first and second support members 345, 348 includes a rectangular shaped body 380, 382 respectively which extends in a direction substantially parallel to the longitudinal axis B-B, the body having first and second spaced apart-faces 386, 388 and 390, 392 respectively, each face lying in a plane which is parallel to the plane defined by the panel. Each body further includes third and fourth spaced-apart faces 394, 396 and 398, 400, each face lying in a plane which is perpendicular to the plane defined by the panel. The body portion 380, 382 of each support member includes a bottom surface 402, 404 forming a respective first end thereof, each bottom surface being connected to the upper surface of the c-shaped body of the stop member, and a top surface 406, 408 forming a respective second end of the body of each support member.

Figure 10:
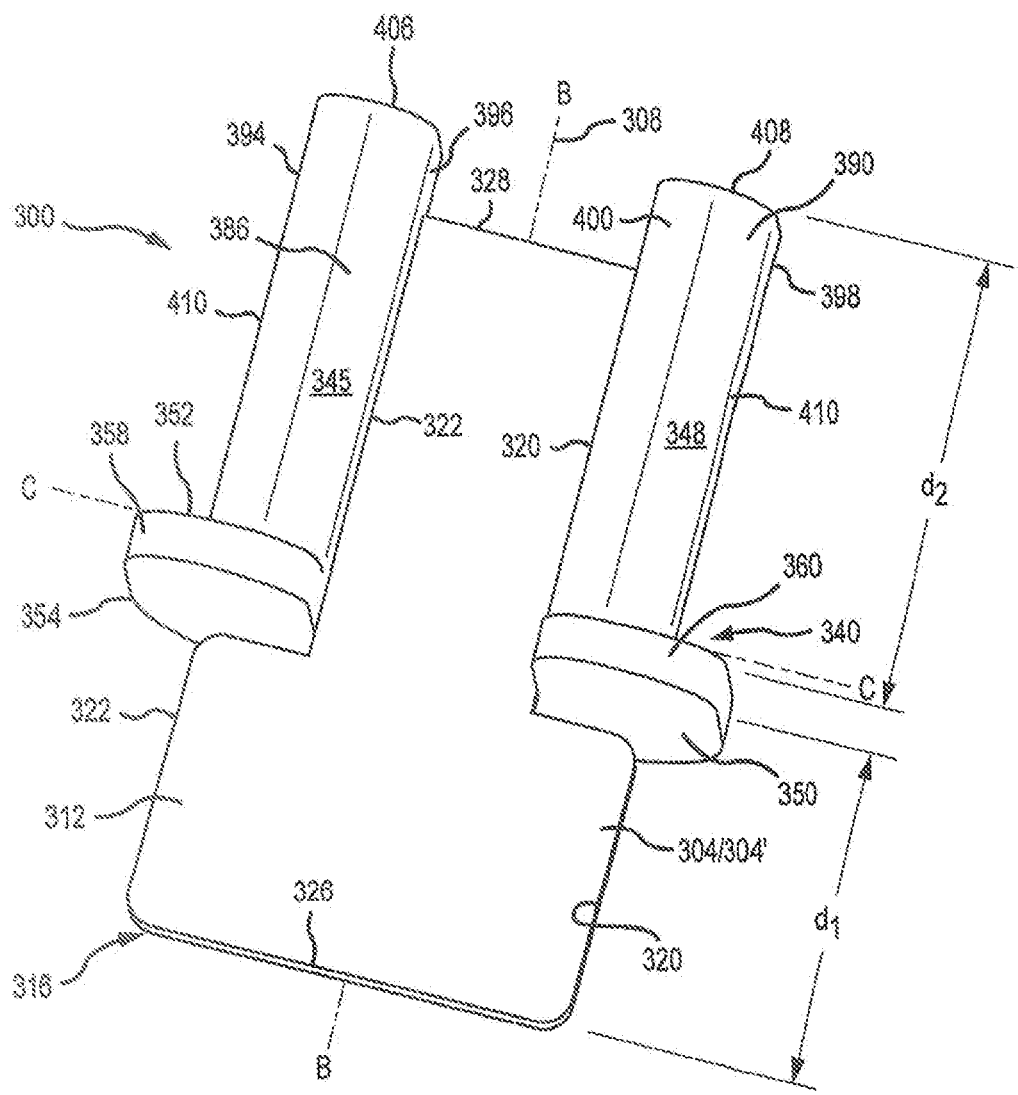
FIG. 10 is a bottom perspective view of a bite block in accordance with an embodiment.
Figure 11:
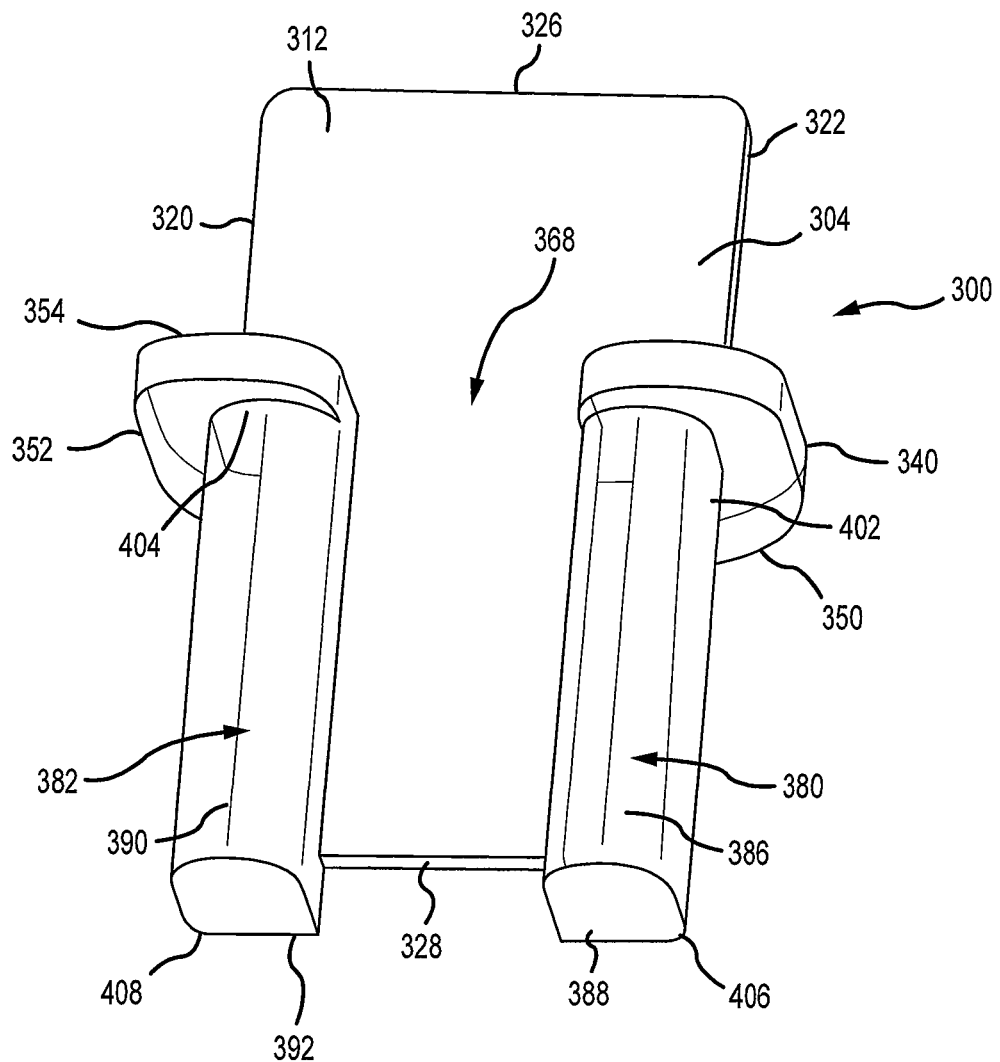
FIG. 11 is a bottom perspective view of the bite block shown in FIG. 10 in accordance with an embodiment.
Figure 12:
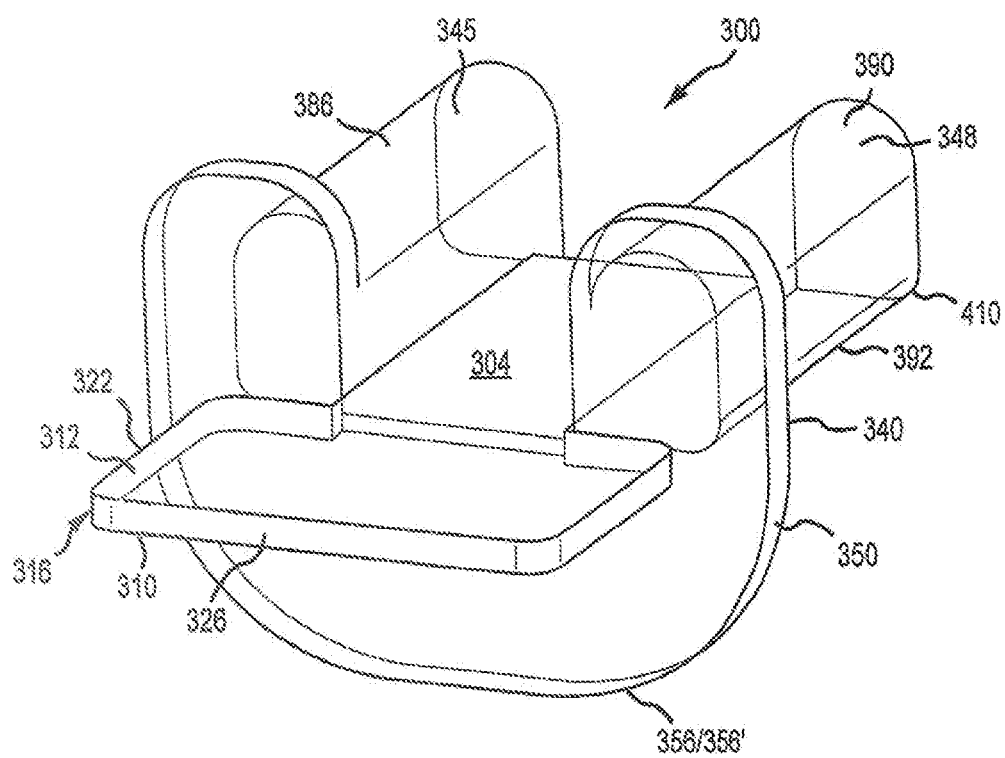
FIG. 12 is a bottom perspective view of the bite block shown in FIG. 10 enlarged to more clearly illustrate the elements thereof.
Figure 13:
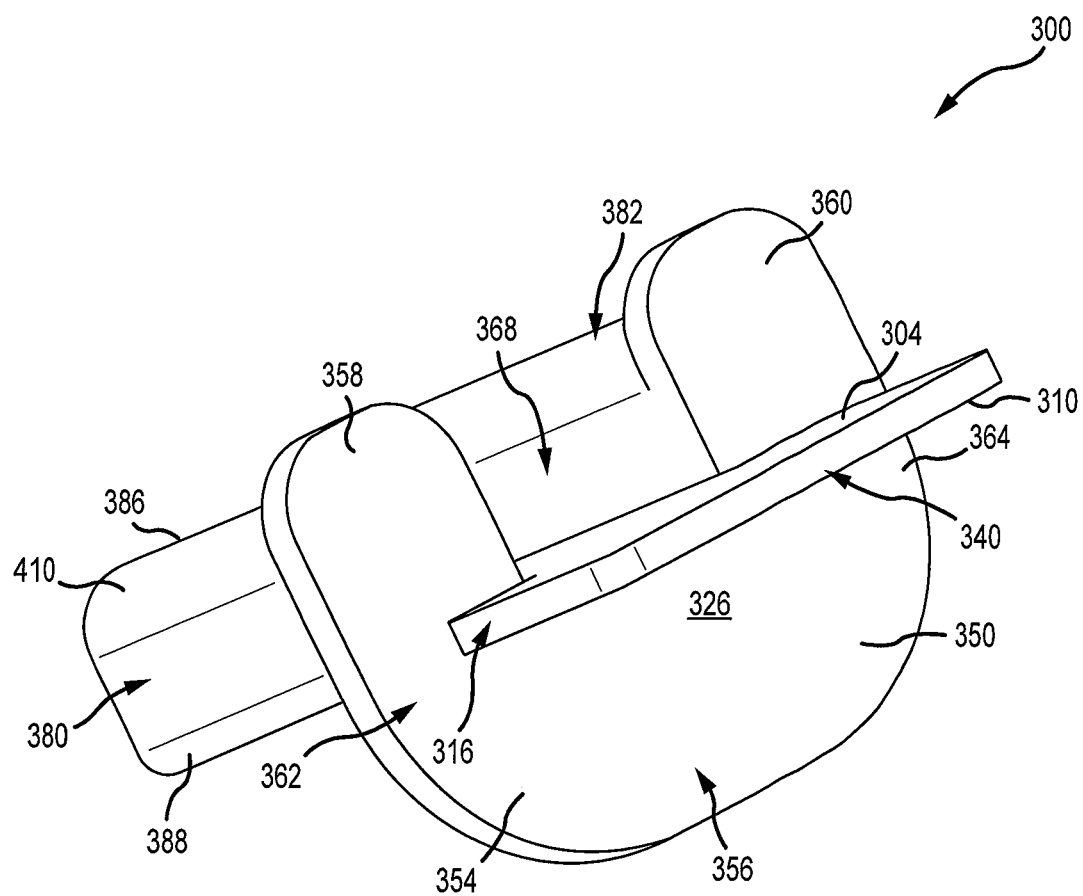
FIG. 13 is still another bottom perspective view of the bite block shown in FIG. 10.

As best illustrated in FIG. 10, the top surfaces 406, 408 of each of the first and second support members lie in a plane extending in a direction parallel to the plane of the c-shaped body 350 of the stop member and is located at a distance $d_2$ from the upper surface of the stop member. In the embodiment shown, the distance $d_2$ between the plane of the upper surfaces of the support members and the upper surface of the stop member is greater in a proximal direction than a corresponding distance $d_1$ between the transverse edge 328 of the plate 304 and the lower surface of stop member. However, other distances or spacing may be employed without departing from the scope of the instant invention. The rectangular shaped body of each of the support members further includes four edges 410, each edge extending in a direction substantially parallel to the longitudinal axis B-B of the bite block. Each of the four edges 410 may be rounded as shown to enhance a patient's comfort level when the bite block is installed in the patient's oral cavity, as shown in FIGS. 14 and 15.

As shown in FIGS. 2 and 3, the airway device and retention member 100 are placed in the tower structure in a level such as to ensure that when a reasonably sized airway device 5 is properly positioned in a patient's trachea, the retention member ribs 105 will reside outside the patient's oral cavity and at least two ribs of the retention collar will interface with the recesses of the restraining tower 60. The airway stabilization system herein disclosed is designed to ensure that a maximum number of ribs 105 are enclosed within the stabilizer restraining tower 30 when the physician chooses a reasonably sized tube and properly positions the tube by placing the endotracheal tube while monitoring the positions of the reflective locator bands 255 and the depth reference markers or indicators 264. If the airway device and attached retention member is positioned in the tower structure with less than two ribs interfacing with the recess in the tower, the stop member 166 will prevent closure of the two c-shaped collars 64, 66, thus requiring proper repositioning of the apparatus.

Following positioning of an airway device 5 in a patient's trachea at a correct depth, the securing apparatus 30 as herein described may be releasably attached to the airway device via releasable engagement with the retention member or collar 100 secured thereto. The relative position of the retention member, and, accordingly, the airway device, in relation to the relative position of the securing apparatus, may be monitored to ensure that the relative positions do not change by observing the position of the at least one marked middle rib 106 on the collar 100 with respect to the spaced apart reference markings or depth guides 79 on c-collar 64. Should a change in these relative positions be observed, the practitioner may depress the quick-release actuator or button 77 to easily open the collars and adjust the relative positions of the stabilizer and the collar without interrupting ventilation of the patient.

In field emergency situations such as those that may be encountered by backcountry paramedics, ski patrol personnel, and military medics in combat situations, for example, the airway stabilization apparatus of the embodiments of FIG. 1, et seq. may not be readily available and may not be included as part of routinely carried field gear due to size and weight limitations. Accordingly, a relatively small, compact and lightweight intubation and airway stabilization system that could be carried into remote areas in a field emergency first aid pack, a fanny pack or even in a pocket of a field jacket or field pants could save an accident victim's life while awaiting evacuation to a trauma facility.

Figure 5:
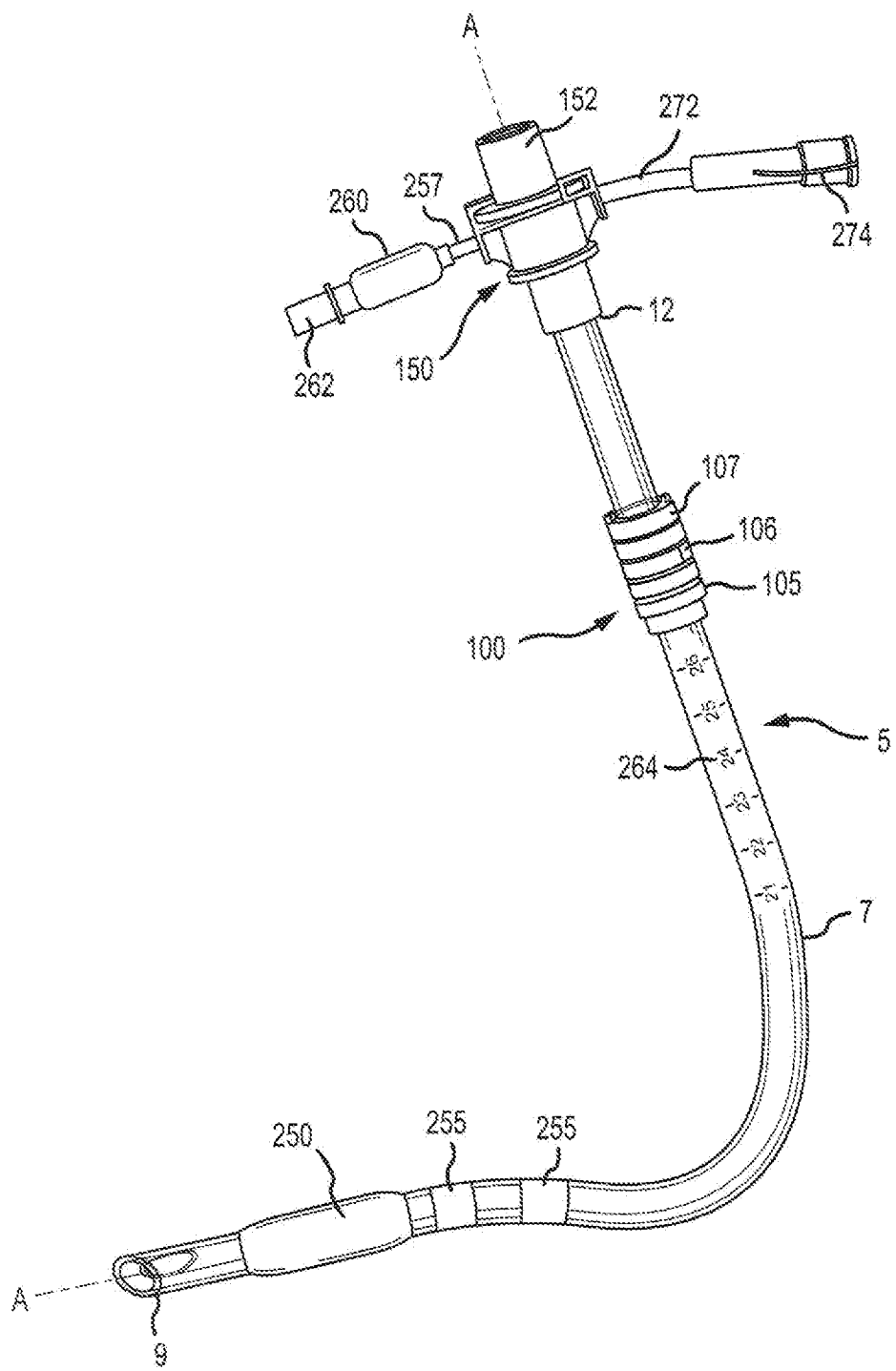
FIG. 5 is a side perspective view of the airway device of FIG. 4 embodiment conformed anatomically to an exemplary patient's trachea in accordance with an embodiment.
Figure 16:
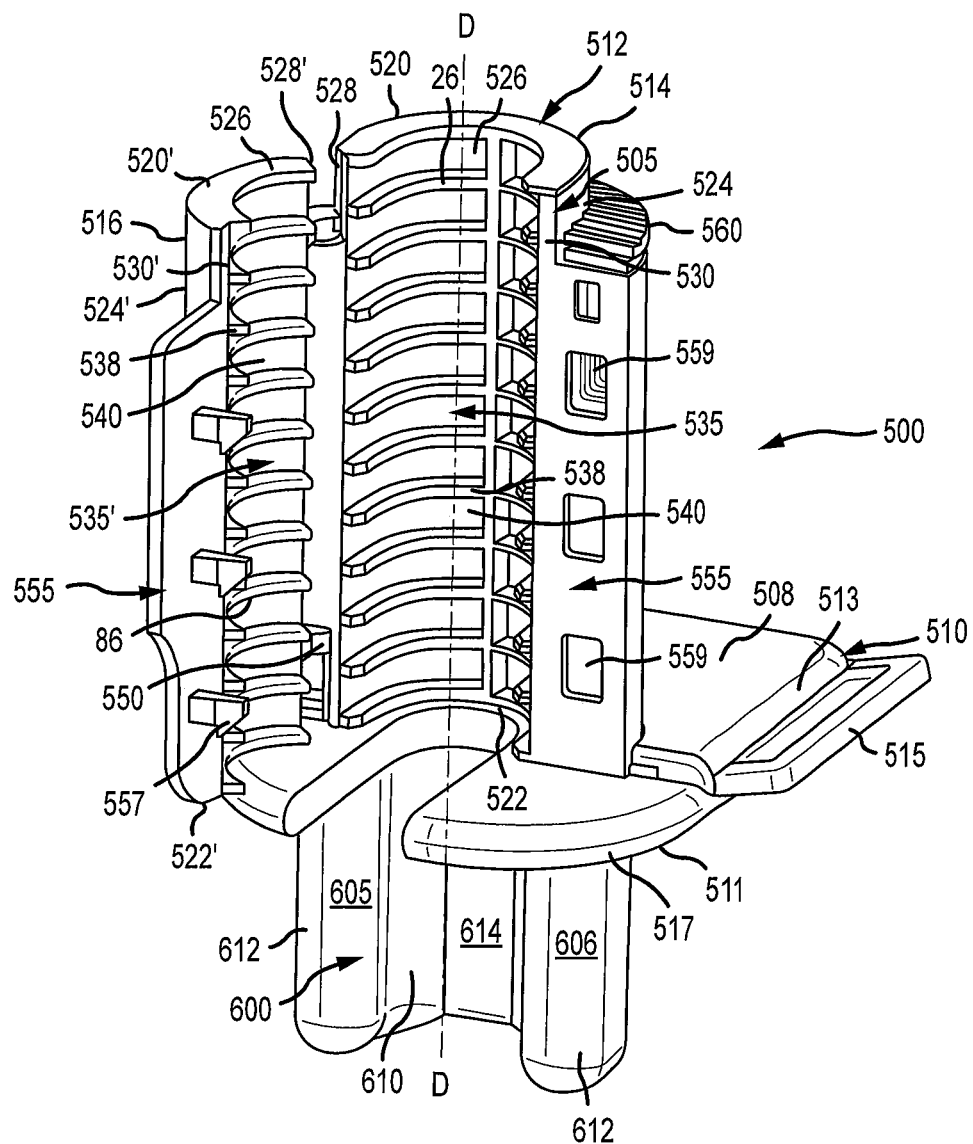
FIG. 16 is a side perspective view of a securing apparatus or stabilizer to an embodiment of the present invention.

Referring to FIG. 16, a field emergency stabilization and securing apparatus 500 is illustrated which meets the foregoing needs and which may be used with an exemplary airway device such as the device 5 shown in FIGS. 1, 4 and 5. The securing apparatus includes a generally cylindrically-shaped tower structure 505 extending in a substantially perpendicular direction from a top surface 508 of a plate 510 along axis D-D, the tower structure including a body portion 512 having a length l and comprising a pair of oppositely disposed, pivotally interconnected, c-shaped collars 514, 516 respectively extending generally symmetrically about and along the axis D-D in a direction away from the patient's face when installed on a patient. Each of the collars has a length l, first and second end portions 520, 520' and 522, 522', an outer surface 524, 524', an inner surface 526, 526'. Similar in construction to the tower of the embodiment of FIG. 1, each of the outer and inner surfaces extends intermediate the c-shaped collars' respective first and second end portions. Each of the collars has a pair of generally parallel extending edge surfaces 528, 530 and 528', 530', the edge surfaces and the corresponding c-shaped collar each defining a semi-cylindrically shaped cavity 535, 535' about the axis D-D. These cavities are most clearly shown in FIG. 16 from the side and in FIG. 20 from the top.

Each c-shaped collar includes a plurality of substantially uniformly spaced-apart annular flanges 538 positioned axially along the respective inner surfaces thereof and extending substantially inwardly therefrom, and a plurality of structural recesses 540 positioned axially along each inner surface intermediate an adjacent two of the plurality of substantially uniformly spaced-apart annular flanges, each one of the plurality of annular flanges cooperating with an adjacent one of the plurality of annular flanges to define one of the plurality of structural recesses. Each of the annular flanges has an aperture 542 formed therein, each aperture being adapted to receive the airway device 5 and a retention member 100 installed thereon, as described above.

In operation, the collars 514 and 516 are pivotally interconnected, for example, by hinge member 550 and are moveable into mating contact with one another, thereby forming a cavity 552 when closed and adapted to releasably engage the retention member secured to the airway device. Each of the c-shaped collars includes a snap, clip, latch, camming operating apparatus or other suitable interlocking feature 555 having one or more locking members 557 adapted to releasably engage corresponding mating locking members 559 formed in or secured to the other c-shaped collar to releasably clamp them together circumferentially around the airway device in stabilizing and supporting engagement therewith. A release mechanism, for example, a quick-release actuator or button 560, allows the c-collars to be easily and rapidly released from locking engagement with one another to facilitate positioning and adjustment of the plate and cylindrically-shaped tower structure with respect to the retention member 100.

Once the airway device is positioned at the desired depth in a patient's trachea, the strap 35 of the securing apparatus described above is secured around the patient's head. The plate 510 is preferably of unitary construction and may be formed integrally with the tower structure or secured thereto by suitable adhesive bonding methods. The tower and plate may be formed of plastic, rubber, metal, composite material or other suitable materials having the desired physical properties for the application. As described above, the plate 510 includes an upper or top surface 508, an oppositely disposed lower or bottom surface 511, the upper and lower surfaces being interconnected by a peripherally extending edge 517 and a pair of oppositely disposed, spaced apart end portions 513, each end portion having an aperture or slot 515 formed therein and adapted to receive strap or securing apparatus 35.

Figure 20:
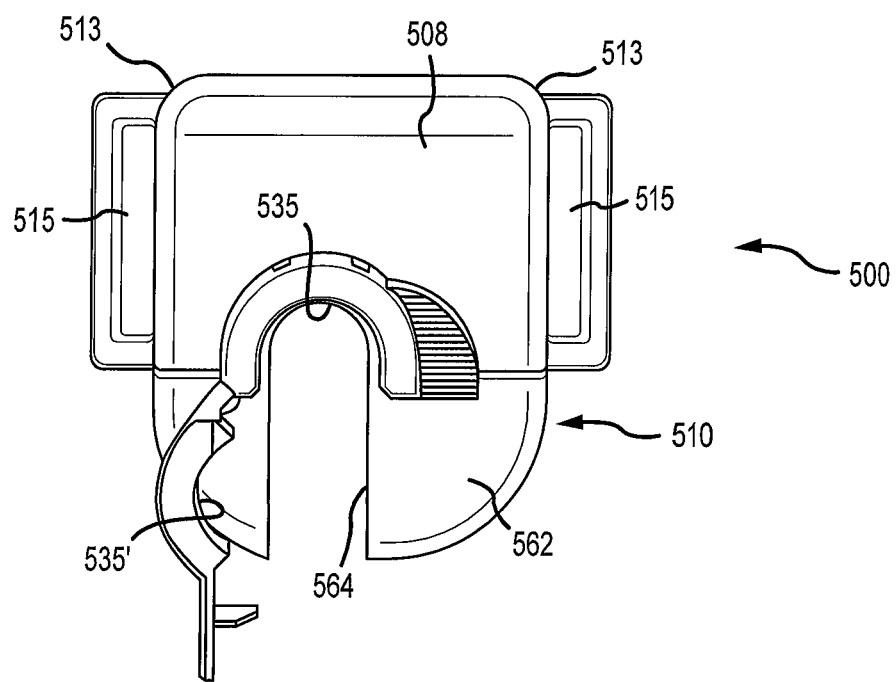
FIG. 20 Is a top plan view of the securing apparatus or stabilizer of FIG. 16.

As seen most clearly in FIG. 20, the plate 510 includes a generally semicircular end portion 562 having a slot 564 formed therein and adapted to releasably receive an airway device 5. This feature permits the securing apparatus to be affixed to a pre-intubated patient from the side, as noted earlier with other embodiments, without being placed over the end of the device requiring disconnection of the airway device from a source of ventilatory air.

When the c-collars 514 and 516 are locked together, the inwardly extending annular flanges 538 and structural recesses 540 on the inner surfaces of the c-shaped collars releasably engage corresponding mating structural recesses 107 and outwardly extending spaced-apart ribs 105 of the retention member (FIG. 4), thereby creating multiple points of contact and interaction between the securing apparatus and the airway device and thus preventing clinically significant movement of the airway device in response to substantial forces which may be applied thereto in any direction. The retention structure and securing apparatus cooperate to completely enclose the airway device whereby the airway device is isolated totally from any constricting, pinching, or crushing forces that would constrict an inner diameter thereof, thereby also restricting ventilation of a patient.

Figure 17:
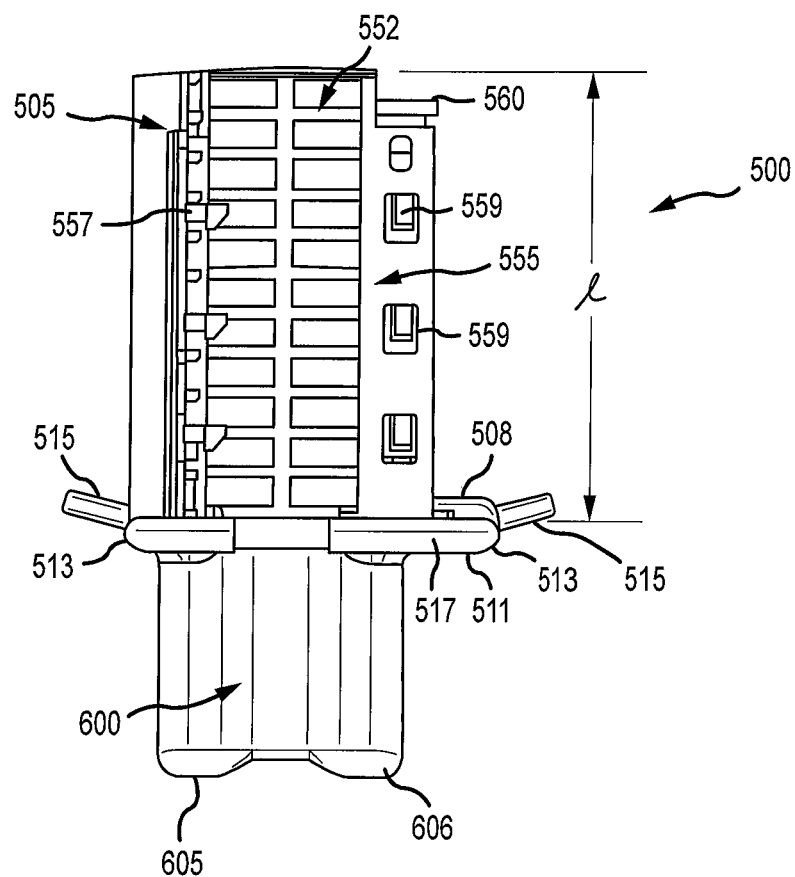
FIG. 17 is a front elevation view of the securing apparatus or stabilizer of FIG. 16 show in an open position to more clearly illustrate the elements thereof.
Figure 18:
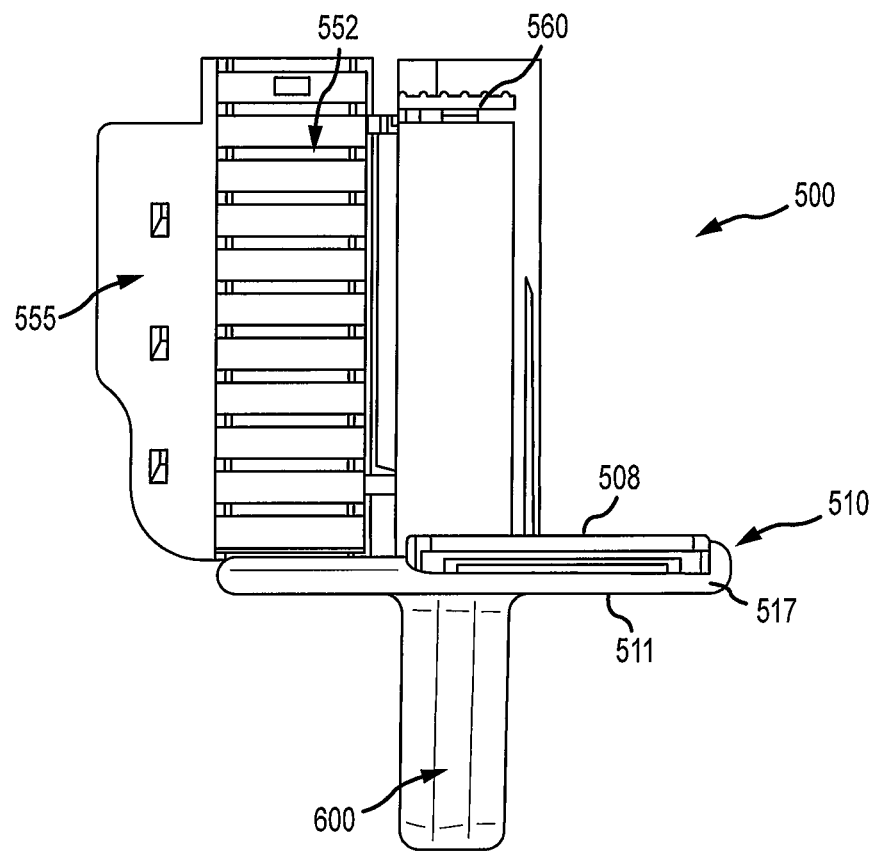
FIG. 18 is a right side elevation view of the securing apparatus or stabilizer of FIG. 16.
Figure 19:
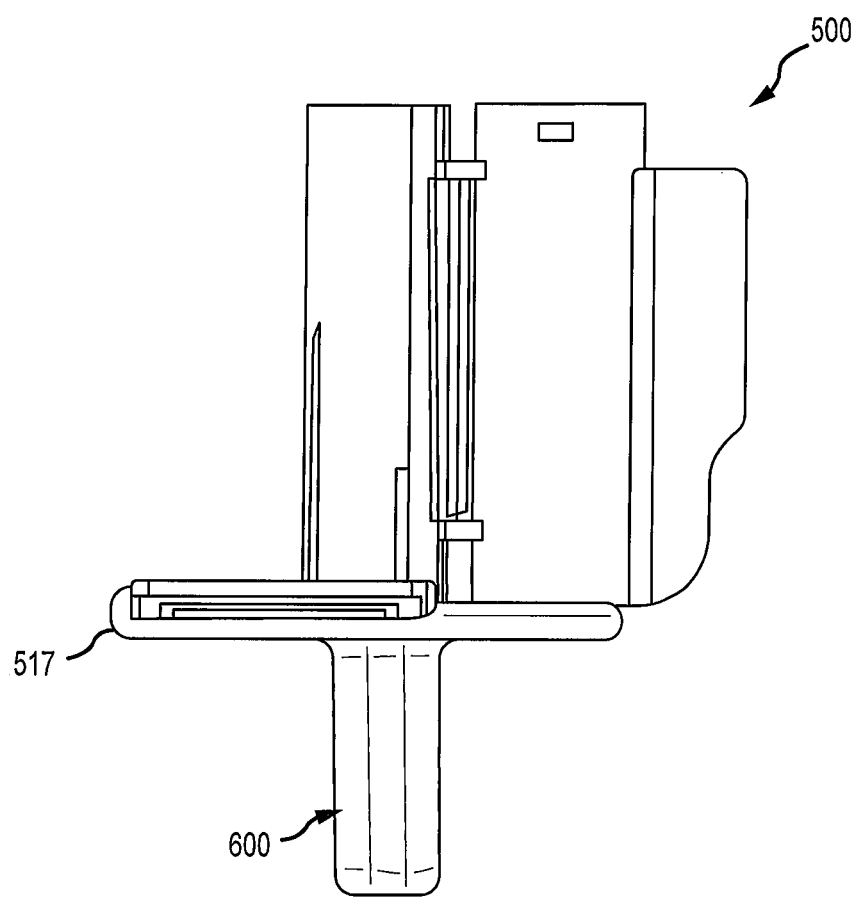
FIG. 19 is a left side elevation view of the securing apparatus or stabilizer of FIG. 16.
Figure 21:
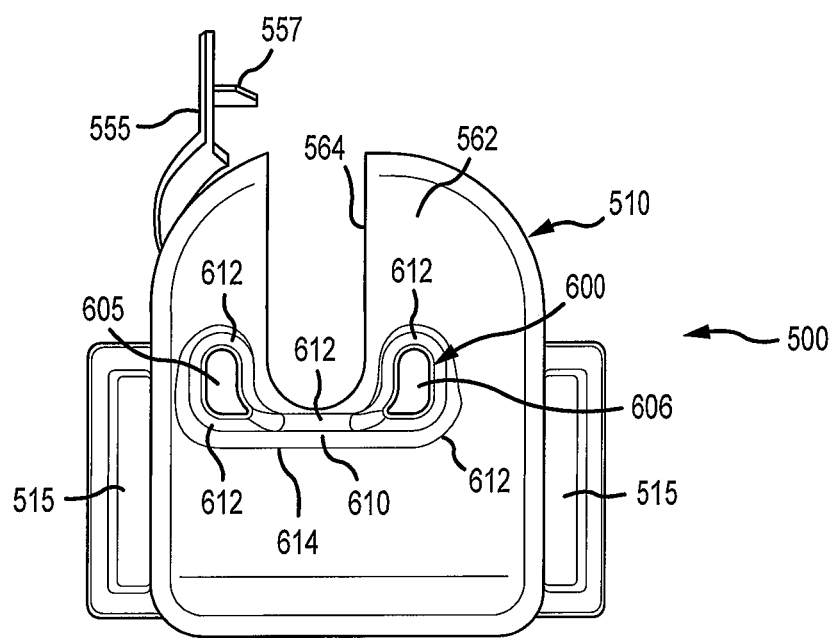
FIG. 21 is a bottom plan view of the securing apparatus or stabilizer of FIG. 16.

Referring now to FIGS. 16, 17 and 21, a bite block 600 formed integrally with or secured to the plate of the securing apparatus 500 is shown. The bite block includes a first and a second support member 605 and 606, each extending parallel to the longitudinal axis D-D and being separated by a panel or spacer 610 extending therebetween in a direction parallel to axis D-D. Each of the support members includes a plurality of segments 612 operatively interconnected and structured and arranged to form a generally curvilinear outer surface 614 of the bite block. As illustrated in FIG. 21, the curvilinear surface is adapted to permit ease of positioning of the bite block in a patient's oral cavity and to enhance the patient's comfort level while the securing apparatus and endotracheal tube are installed and further cooperates with the slot 564 formed in the semicircular end portion in releasably receiving an airway device from the side. The plate 510 also serves as a transversely extending stop member in the same manner as stop member 340 of the embodiment of FIG. 10.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An airway stabilization system for maintaining an airway in a human or animal patient's trachea, the patient having a head, a face, a nose, cheeks, a mouth, lips, an oral cavity, a chin, a larynx, and a carina, the system comprising:

an airway device adapted to conform anatomically to the patient's trachea when positioned therein, the airway device including a flexible elongate body extending along an axis and having a length, an internal diameter and an external diameter, a distal end portion, and a proximal end portion and a continuous sidewall having an internal surface and an external surface extending between the proximal and the distal ends, the flexible elongate body of the airway device including a plurality of insertion depth reference markers affixed to the proximal end thereof;

a respiratory connector adapted to connect the airway device to an external source of ventilatory air;

a retention member positioned on the airway device and extending circumferentially about and coaxially along the body portion of the airway device, the retention member having a length and including a plurality of uniformly spaced-apart ribs positioned axially along the length of the retention member and extending radially outwardly therefrom, the retention member further including a plurality of structural recesses positioned axially along the length of the retention member, each of the plurality of structural recesses being positioned intermediate an adjacent two of the plurality of spaced-apart ribs;

a securing apparatus adapted to be secured to the patient, the securing apparatus including a faceplate having an upper or top surface, a lower or bottom surface, and a cylindrically-shaped tower structure extending in a perpendicular direction from the top surface coaxially with the axis, the tower structure including a body portion having a length and comprising a pair of oppositely disposed, pivotally interconnected, c-shaped collars respectively extending symmetrically about and along the axis in a direction away from the patient's face when installed on a patient, each of the collars having a length, first and second end portions, an outer surface, an inner surface, each of the outer and inner surfaces extending intermediate the first and second end portions, a pair of parallel extending edge surfaces and defining a semi-cylindrically shaped cavity about the axis, a hinge member operatively connected to each of the c-shaped collars along one of the pair of parallel extending edge surfaces whereby each of the c-shaped collars is pivotably movable into mating contact with one another along each of the pair of parallel extending edge surfaces defining a cavity, the cavity having an inner diameter C, each c-shaped collar including a plurality of uniformly spaced-apart annular flanges positioned axially along the inner surface of the body portion and extending inwardly therefrom, a plurality of structural recesses positioned axially along the inner surface of the body portion intermediate an adjacent two of the plurality of uniformly spaced-apart annular flanges, each one of the plurality of annular flanges cooperating with an adjacent one of the plurality of annular flanges to define one of the plurality of structural recesses, each of the plurality of annular flanges including an aperture formed therein, each aperture being adapted to receive the airway device and the retention member when installed thereon;

a connector assembly operatively connected to the proximal end of the elongate body of the airway device, the connector assembly being adapted to connect the respiratory connector to the airway device and including a body extending along the axis and having a length, an internal diameter and an external or outer diameter, a distal end portion adapted to receive the proximal end of the airway device, a proximal end portion adapted to receive the respiratory connector, a continuous sidewall extending between the proximal and the distal ends, a safety stop member extending radially outwardly from the continuous sidewall, the stop member including a flange extending circumferentially around the continuous sidewall of the connector assembly body and defining a first plane which is perpendicular to the axis, the flange having an outer diameter which is larger than both the outer diameter of the connector assembly body and the inner diameter C of the cavity defined by the pivotally movable c-shaped collars, the safety stop member being adapted to cooperate with the pivotally interconnected, c-shaped collars respectively whereby the safety stop member prevents closure thereof when the airway device is improperly positioned too low in the cavity, and a locking device secured to the proximal end, the locking device being structured and arranged to releasably secure the respiratory connector to the connector assembly, and a connector portion extending proximally along the axis from the safety stop member, the connector portion being adapted to removably receive the respiratory connector; and a strap adapted to be releasably secured about the patient's head and to releasably secure the securing device to the patient when it is installed.

2. The airway stabilization system of claim 1 wherein at least one of the plurality of ribs formed on the retention structure is marked to distinguish it from the other of the plurality of ribs formed thereon.

3. The airway stabilization system of claim 2 wherein the locking device includes a plate member having an upper surface and a lower surface, the lower surface being secured to the proximal end of the connector assembly, the upper surface including first and second locking channels or pockets attached thereto, and a centrally-positioned aperture extending intermediate the upper and lower surfaces along the axis, the aperture having a diameter the same as the external diameter of the airway device.

4. The airway stabilization system of claim 3 wherein the plate member defines a second plane which is perpendicular to the axis and positioned proximally above the first plane of the stop member, the plate member further including an edge surface extending intermediate the upper and lower surfaces of the plate member in a direction parallel to the axis.

5. The airway stabilization system of claim 4 wherein the respiratory connector comprises a tubular member having an air passage extending therethrough along the axis, a proximal end configured to be secured to a source of ventilatory air, at least one locking flange extending radially outwardly from the proximal end defining a third plane which is perpendicular to the axis, and a distal or connector end operatively connected to the at least one locking flange and extending distally therefrom along the axis, the connector portion being adapted to be removably inserted into the proximal end of the central connector.

6. The airway stabilization system of claim 5 wherein the at least one locking flange includes a rectangular shaped plate member having a pair of oppositely disposed long and short edges, one of the long edges being secured to the distal end of the tubular member and the other of the long edges cooperating with each of the short edges to form a pair of rounded corners, at least one of the pair of corners being structured and arranged to facilitate rotational insertion thereof into and to releasably engage one of the first and second locking channels or pockets attached to the upper surface of the plate member of the locking device.

7. The airway stabilization system of claim 6 wherein the respiratory connector includes a second locking flange extending outwardly from the distal end of the respiratory connector in the plane defined by the first locking flange and in a radially opposite direction from the direction of the first locking flange.

8. The airway stabilization system of claim 7 wherein the second locking flange includes a rectangular shaped plate member having a pair of oppositely disposed long and short edges, one of the pair of long edges being secured to the distal end of the tubular member and the other of the pair of long edges cooperating with each of the short edges to form a pair of rounded corners, at least one of the corners being structured and arranged to facilitate rotational insertion thereof into and to releasably engage the second of the first and second locking channels or pockets attached to the upper surface of the plate member of the locking device.

9. The airway stabilization system of claim 8 further including a balloon secured to the distal end of the airway device, an inflation tube or line adapted to inflate the balloon to a preselected pressure range, the inflation tube being operatively connected at a first end thereof to a source of inflationary air and at a second end thereof to an ingress aperture formed in the contiguous sidewall of the inflation device at the proximal end thereof, an inflation lumen formed in the continuous sidewall of the airway device and extending from the ingress aperture the length of the airway device's body portion to n egress aperture formed in the distal end of the airway device, the egress aperture being in fluid communication with the balloon, whereby inflationary air is delivered to the balloon.

10. The airway stabilization system of claim 9 wherein the plate member of the locking device of the central connector incudes a radially outwardly extending aperture formed therein extending from the centrally-positioned aperture in the plate to the edge surface extending intermediate the upper and lower surfaces of the plate member, the radially outwardly extending aperture being adapted to receive the inflation tube therein.

11. The airway stabilization system of claim 10 further including a subglottic suction line or tube having a first end connected to a suction apparatus, a body portion extending along the airway device and a second end connected to a suction lumen positioned above the balloon.

12. The airway stabilization system of claim 11 wherein the plate member of the locking device of the central connector incudes a radially outwardly extending aperture formed therein extending from the centrally-positioned aperture in the plate to the edge surface extending intermediate the upper and lower surfaces of the plate member, the radially outwardly extending aperture being adapted to receive the suction tube therein.

13. The airway stabilization system of claim 12 further including a plurality of reflective locator bands proximally positioned with respect to the balloon on and extending circumferentially around the flexible elongate body of the airway device.

14. The airway stabilization system of claim 13 wherein the flexible elongate body of the airway device further includes a plurality of insertion depth reference markers affixed to the proximal end thereof.

15. The airway stabilization system of claim 14 wherein at least one of the pivotally interconnected c-shaped collars includes a plurality of spaced apart depth indicator markings formed thereon, the markings being structured and arranged to cooperate with at least one marked rib formed on the retention structure to indicate the relative position of the retention structure with respect to the position of the restraining device, whereby the relative positions of the retention structure and the restraining device may be monitored to ensure that the relative positions do not change.

16. The airway stabilization system of claim 15 further including a locking mechanism adapted to releasably clamp the pivotally interconnected c-shaped collars together circumferentially around the retention structure.

17. The airway stabilization system of claim 16 wherein the locking mechanism includes a quick release actuator structured and arranged to release the pivotally interconnected c-shaped collars after they have been clamped together.

18. The airway stabilization system of claim 1 wherein the faceplate includes at least one aperture formed therein to permit access to a patient's oral cavity.

19. The airway stabilization system of claim 1 wherein the airway device is a supraglottic airway device.

20. A field emergency airway stabilization and securing apparatus comprising:
- a plate having an upper surface, an oppositely disposed lower surface, the upper and lower surfaces being interconnected by a peripherally extending edge and a pair of oppositely disposed, spaced apart first and second end portions, each end portion having an aperture or slot operatively connected thereto and adapted to receive a securing apparatus, a third semicircular end portion extending intermediate the first and second end portions, the third end portion including a slot adapted to releasably receive an airway device;
- a cylindrically shaped tower structure extending in a perpendicular direction from the top surface of the plate along a longitudinal axis, the tower structure including a body portion having a length/and a pair of oppositely disposed, pivotally interconnected, c-shaped collars extending generally symmetrically about and along the longitudinal axis in a direction away from a patient's face when installed on the patient, each of the c-shaped collars including first and second end portions, an outer surface, an inner surface, each of the outer and inner surfaces extending intermediate the respective first and second end portions of each of the collars, each collar further including a pair of generally parallel extending edge surfaces, the edge surfaces and the corresponding c-shaped collar each defining a semi-cylindrically shaped cavity about the longitudinal axis;
- a plurality of uniformly spaced-apart annular flanges operatively connected to and positioned axially along the respective inner surfaces of each of the collars and extending substantially inwardly therefrom, each of the plurality of spaced apart annular flanges including an aperture adapted to receive the airway device;
- a plurality of structural recesses positioned axially along each inner surface intermediate an adjacent two of the plurality of substantially uniformly spaced-apart annular flanges,
- each one of the plurality of annular flanges cooperating with an adjacent one of the plurality of annular flanges to define one of the plurality of structural recesses;
- a bite block operatively connected to the plate of the securing apparatus, the bite block including a first and a second support member operatively connected to the lower surface of the plate and extending in a direction parallel to the longitudinal axis;
- a panel or spacer positioned intermediate the first and second support members and extending from the lower surface of the plate in a direction parallel to the longitudinal axis; and
- a securing mechanism including one or more locking members adapted to releasably clamp the c-shaped collars in locking engagement with one another; and
- a release mechanism for releasing the c-shaped collars from locking engagement.

\* \* \* \* \*